United States Patent
Jeschke et al.

(10) Patent No.: US 6,265,537 B1
(45) Date of Patent: Jul. 24, 2001

(54) THIODEPSIPEPTIDES FOR COMBATING ENDOPARASITES AND A METHOD FOR PRODUCING THE SAME

(75) Inventors: Peter Jeschke, Leverkusen; Achim Harder, Köln; Georg von Samson-Himmelstjerna, Solingen; Norbert Mencke, Leverkusen; Gerhard Bonse, Köln, all of (DE); Katsuharu Iinuma; Osamu Sakanaka, both of Kanagawa-Ken (JP)

(73) Assignees: Bayer Aktiengesellschaft, Leverkusen (DE); Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/381,946

(22) PCT Filed: Mar. 20, 1998

(86) PCT No.: PCT/EP98/01628

§ 371 Date: Sep. 27, 1999

§ 102(e) Date: Sep. 27, 1999

(87) PCT Pub. No.: WO98/43965

PCT Pub. Date: Oct. 8, 1998

(30) Foreign Application Priority Data

Apr. 2, 1997 (DE) .............................. 197 13 626

(51) Int. Cl.$^7$ ............................. C07K 5/06; C07K 5/00; A61K 38/00
(52) U.S. Cl. ................. 530/317; 530/300; 530/330; 514/16; 514/18
(58) Field of Search ................... 530/300, 317, 530/330; 514/16, 18

(56) References Cited

U.S. PATENT DOCUMENTS

| | | | |
|---|---|---|---|
| 4,231,953 | 11/1980 | Henrick et al. | 260/464 D |
| 4,243,819 | 1/1981 | Henrick et al. | 562/433 |
| 4,411,912 | 10/1983 | Henrick et al. | 424/304 |
| 5,514,773 | 5/1996 | Nishiyama et al. | 530/317 |
| 5,646,244 | 7/1997 | Nishiyama et al. | 530/317 |
| 5,663,140 | 9/1997 | Scherkenbeck et al. | 514/11 |
| 5,747,448 | 5/1998 | Ohyama et al. | 514/11 |

*Primary Examiner*—Rodney P Swartz
*Assistant Examiner*—Padma Baskar
(74) *Attorney, Agent, or Firm*—Joseph C. Gil; Godfried R. Akorli

(57) ABSTRACT

The present invention relates to cyclic thiodepsipeptides, in particular 18 to 24-membered cyclothiodepsipeptides, their endoparasitical compositions, and methods of making and using the same.

10 Claims, No Drawings

THIODEPSIPEPTIDES FOR COMBATING ENDOPARASITES AND A METHOD FOR PRODUCING THE SAME

The present invention relates to cyclic thiodepsipeptides, in particular 18- to 24-membered cyclothiodepsipeptides, to a simple process for their preparation and to their use for controlling endoparasites.

The preferred structural variations of biologically active peptides include the ex-change of amide-oxygen for sulfur, since the thioamide group (Ψ[CSNH]) shows a pronounced isosterism to the amide group (CONH) (cf. for example B. D. B. Sherman et al., J. Amer. Soc. 112, 1990, p. 433; M. Kajtar et al., Tetrahedron 42, 1986, p. 3931; D. J. S. Guthrie et al., Int. J. Peptide Protein Res. 28, 1986, p. 208). However, it is difficult to predict the expected biological potency of the thiopeptide, in spite of the great physical similarity to the parent peptide. (cf. L. Lankiewics et al., Biochem. Biophys. Res. Comnnun. 184, (1), 1992, p. 359).

Methods for preparing various endothiopeptides are known from the literature. By way of example, the thionation strategies for various hormones, such as the neurohypophysio hormone oxytocin, the thyrotropin releasing-hormone (THR), the growth hormone-releasing peptide, and the neuropeptides leucine-enkephalin and demorphine, may be mentioned. (cf. [1-deamino,9-thio-glycine] oxytocin: W. C. Jones et al., J. Amer. Chem. Soc. 95, 1973, p. 5677; thio-TRH: Zs. Majer et al., Biochem. Biophys. Res. Conmmun. 150, 1988, p. 1017; thionated leucine-enkephalines: K. Clausen et al., J. Chem. Soc., Perkin Trans. I 1984, p.785 and Biochem. Biophys. Res. Commun. 120, 1984, p. 305; Thio-demorphin: S. Salvadori et al., Farmaco Ed. Sc., 39, 1984, p. 216; Thio-TRH: M. Kruszynski et al., Experentia 41, 1985, p. 1576).

The authors Ried et al., Mock et al., Campbell et al. or Bartlett et al. worked out further possible syntheses of N-protected endothiodipeptide esters and salts thereof, Brown et al. gained access to N-protected endothiotripeptide esters (cf. W. Ried et al., Angew. Chem. 72, 1960, p. 268; W. L. Mock et al., Biochem. Biophys. Res. Commun. 102, 1981, p. 389; 1973, p. 5677; Campbell et al., J. Amer. Chem. Soc. 104, 1982, p. 5221; P. A. Bartlett et al., 21, 1982, p. 1608; D. W. Brown et al., Tetrahedron 39, 1983, 1075).

Compared to the abovementioned methods for preparing various endothiopeptides, only little is known about the preparation of thiodepsipeptides comprising amino acids, hydroxythiocarboxylic acids and, if appropriate, hydroxycarboxylic acids.

The preparation of some thiol esters of amino acids and their use as insecticides and acaricides are known (cf. DE-A 2812169, C. A. Henrick et al., Pestic. Sci. 11, (2), 1980, p. 224; U.S. Pat. No. 4,243,819, U.S. Pat. No. 4,231,953).

Furthermore, a thiodepsipeptide PM-93135, which was isolated as a fermentation product from a rmicromonospora strain (actinomycetes) and has antibacterial activity, is known (cf. WO 95/277730).

Cyclothiodepsipeptides comprising amino acids, hydroxythiocarboxylic acids and, if appropriate, hydroxycarboxylic acids as ring building blocks have not been disclosed before.

Cyclodepsipeptides having 18 to 24 ring atoms for use as agents for controlling endoparasites are known (cf. for example B. Y. Kodama et al., Sci. Reports of Meiji Seika Kaisha 31, 1992, p. 1–8; EP-A 382 173; EP-A 503 538; WO 93/19 053; WO 94/19334; WO 95/07272; EP 626 375; EP 626 376; EP 664 297; EP 634 408; 718 298).

The present invention, accordingly, provides novel cyclic thiodepsipeptides and a process for preparing the cyclic thiodepsipeptides comprising amino acids, hydroxythiocarboxylic acids and, if appropriate, hydroxycarboxylic acids as ring building blocks and 18 to 24 ring atoms.

The use of cyclic thiodepsipeptides comprising amino acids, hydroxythiocarboxylic acids and, if appropriate, hydroxycarboxylic acids as ring building blocks and 18–24 ring atoms for use as agents for controlling endoparasites also form part of the subject matter of the invention.

The present invention provides in particular:

1. Cyclic thiodepsipeptides of the general formula (I) and salts thereof

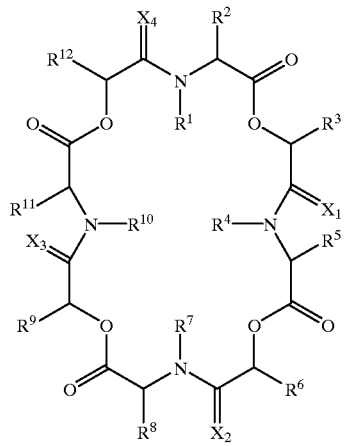

(I)

in which $R^1$, $R^4$, $R^7$ and $R^{10}$ each represent independently of one another hydrogen, straight-chain or branched $C_{1-4}$-alkyl, $R^2$, $R^5$, $R^8$ and $R^{11}$ each represent independently of one another hydrogen, straight-chain or branched $C_{1-8}$-alkyl, $C_{1-8}$-alkenyl, $C_{3-6}$-cycloalkyl, $C_{3-6}$-cycloalkyl-$C_{1-2}$-alkyl, aryl-$C_{1-2}$-alkyl, hetaryl-$C_{1-2}$-alkyl, aryl or hetaryl, each of which is optionally substituted, $R^9$ and $R^{10}$ together with the atoms that they are attached to represent a 5- or 6-membered ring which may optionally be substituted, $R^{10}$ and $R^{11}$ together with the atoms that they are attached to represent a 5-, 6- or 7-membered ring which may optionally be interrupted by oxygen, sulfur, sulfoxy or sulfonyl and may optionally be substituted, $R^3$ and $R^9$ each represent independently of one another hydrogen, $C_{1-8}$-alkyl or aryl-$C_{1-2}$-alkyl, $C_{3-6}$-cycloalkyl-$C_{1-2}$-alkyl, $R^6$ and $R^{12}$ each represent independently of one another hydrogen, straight-chain or branched $C_{1-8}$-alkyl, $C_{1-8}$-alkenyl, $C_{3-6}$-cycloalkyl, $C_{3-6}$cycloalkyl-$C_{1-2}$-alkyl, aryl-$C_{1-2}$-alkyl, hetaryl-$C_{1-2}$-alkyl, aryl or hetaryl, each of which is optionally substituted, and $X^1$, $X^2$, $X^3$ and $X^4$ each represent independently of one another oxygen or sulfur, it being necessary for at least one of the radicals $X^1$, $X^2$, $X^3$ and $X^4$ to represent sulfur, and their optical isomers and racemates.

2. The novel cyclic thiodepsipeptides of the general formula (I) and salts thereof (I)

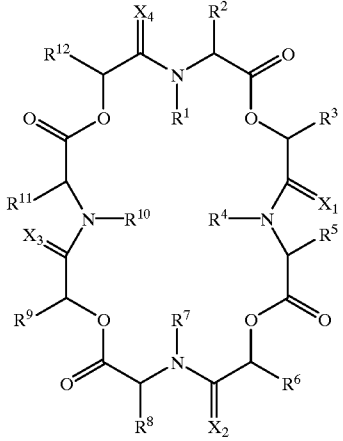

in which

R¹ to R¹² and X¹ to X⁴ are as defined under 1 are prepared by thionating the depsipeptides of the general formula (II) and salts thereof (II)

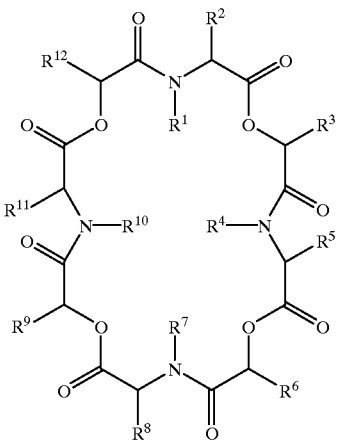

in which

R¹ to R¹² and X¹ to X⁴ are as defined under 1 in the presence of a suitable sulfurizing agent and in the presence of the suitable diluent.

Depending on the kind of the substituents, the compounds of the general formula (I) can be present as mixtures of geometrical and/or optical isomers of various compositions. The invention relates to the pure isomers and also the mixtures of isomers.

Preference is given to cyclic thiodepsipeptides comprising amino acids, hydroxythiocarboxylic acids and optionally hydroxycarboxylic acids as ring building blocks and having 24 ring atoms, of the general formula (I) and salts thereof (I)

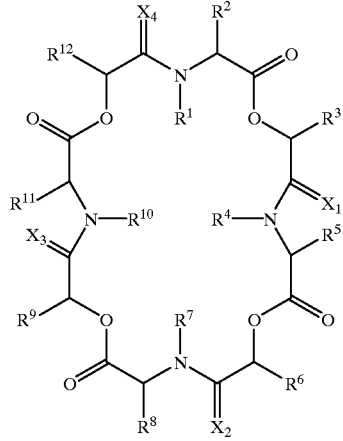

in which $R^1$, $R^4$, $R^7$ and $R^{10}$ each represent straight-chain or branched $C_{1-4}$-alkyl, in particular methyl, $R^2$, $R^5$, $R^8$ and $R^{11}$ each represent $C_{1-4}$-alkyl, in particular isobutyl, $R^3$ and $R^9$ each represent independently of one another $C_{1-4}$-alkyl or aryl-$C_{1-2}$-alkyl, in particular benzyl, $R^6$ and $R^{12}$ each represent independently of one another $C_{1-4}$-alkyl, hetaryl-$C_{1-2}$-alkyl, $C_{1-4}$-alkoxycarbonylmethyl, aryl-$C_{1-2}$-alkyl, in particular benzyl, suitable substituents including hydrogen, halogen, cyano, carbamoyl, $C_{1-4}$-alkyl, hydroxyl or hydroxyl carrying a protecting group, $C_{1-8}$-alkoxy, $C_{1-4}$-alkoxy-$C_{1-4}$-alkoxy, $C_{2-4}$-alkenyloxy, hetaryl-$C_{1-4}$-alkoxy where the heterocycles may in turn be substituted, nitro, amino or amino carrying a protecting group, amino-$C_{1-6}$-alkoxy or amino-$C_{1-6}$-alkoxy carrying a protecting group, n-mono-$C_{1-6}$-alkyl-amino-$C_{1-6}$-alkoxy, N-methylamino-N,N-di-$C_{1-6}$-alkylamino-$C_{1-6}$-alkoxy, N,N-di-[($C_{1-6}$-alkoxy-$C_{1-6}$-alkyl)]amino-$C_{1-6}$-alkoxy, $C_{1-4}$-alkylamino, $C_{1-4}$-dialkylamino, N,N-di[($C_{1-6}$-alkoxy-$C_{1-6}$-alkyl)]amino-sulfonyl, $C_{1-4}$-dialkyl-amino-sulfonyl, sulfamidyl, $C_{3-7}$-cycloalkylamino-$C_{1-6}$-alkylamino-sulfonyl, $C_{3-7}$-cycloalkyl-amino-$C_{1-6}$-alkoxy, $C_{3-7}$-cycloalkylamino-sulfonyl, $C_{3-7}$-cyclo-alkylamino- (where each cycloalkyl may contain one or more nitrogen atoms as ring-forming atoms and additionally oxygen or sulfuir atoms), and (i)
$X^1$ represents sulfur,
$X^2$, $X^3$ and $X^4$ each represent independently of one another oxygen or sulfur, or (ii)
$X^2$ represents sulfur,
$X^1$, $X^3$ and $X^4$ each represent independently of one another oxygen or sulfur, or (iii)
$X^3$ represents sulfur,
$X^1$, $X^2$ and $X^4$ each represent independently of one another oxygen or sulfur,or (iv)
$X^4$ represents sulfur,
$X^1$, $X^2$ and $X^3$ each represent independently of one another oxygen or sulfur, and their optical isomers and racemates.

The thiodepsipeptides and salts thereof according to the invention are defined in a general way by the formula (I).

The thiodepsipeptides and acid addition salts and metal salt complexes thereof according to the invention have good endoparasiticidal, in particular anthelmintic, action and may preferably be used in the field of veterinary medicine.

Optionally substituted alkyl on its own or as part of a radical in the general formulae means straiglht-chain or branched alkyl preferably having 1 to 6, in particular 1 to 4, carbon atoms. Examples include optionally substituted methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethyl-propyl, hexyl, 1-methylpentyl, 2-methyl-pentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and ethylbutyl.

Preference is given to methyl, ethyl, n-propyl, isopropyl, n-butyl, isobutyl, sec-butyl and tert-butyl.

Optionally substituted alkenyl on its own or as part of a radical in the general formulae means straight-chain or branched alkenyl preferably having 1 to 6, in particular 1 to 4, carbon atoms. Examples include optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-bute-nyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl4-pentenyl, 4-methyl4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl- 1-methyl-2-propenyl and 1-ethyl-2-methyl-2-propenyl.

Preference is given to optionally substituted ethenyl, 2-propenyl, 2-butenyl or 1-methyl-2-propenyl.

Optionally substituted alkinyl on its own or as part of a radical in the general formulae means straight-chain or branched aikinyl preferably having 1 to 6, in particular 1 to 4, carbon atoms. Examples include optionally substituted ethinyl, 2-propinyl, 2-butinyl, 3-butinyl, 1-methyl-2-propinyl, 2-pentinyl, 3-pentinyl, 4-pentinyl, 1-methyl-3-butinyl, 2-methyl-3-butinyl, 1-methyl-2-butinyl, 1,1-dimethyl-2-propinyl, 1-ethyl-2-propinyl, 2-hexinyl, 3-hexinyl, 4-hexinyl, 5-hexinyl, 1-methyl-2-pentinyl, 1-methyl-3-pentinyl, 1-methyl-4-pentinyl, 2-methyl-3-pentinyl, 2-methyl-4-pentinyl, 3-methyl-4-pentinyl, 4-methyl-2-pentinyl, 1,1-dimethyl-3-butinyl, 1,2-dimethyl-3-butinyl, 2,2-dimethyl-3-butinyl, 1-ethyl-3-butinyl, 2-ethyl-3-butinyl and 1-ethyl-1-methyl-2-propinyl.

Preference is given to optionally substituted ethinyl, 2-propinyl or 2-butinyl.

Optionally substituted cycloalkyl on its own or as part of a radical of the general formulae means mono-, bi- and tricyclic cycloalkyl preferably having 3 to 10, in particular 3, 5 or 7, carbon atoms. Examples include optionally substituted cyclopropyl, cyclobutyl, cyclopentyl, cyclohexyl, cycloheptyl, cyclooctyl, bicyclo[2.2.1]heptyl, bicyclo[2.2.2]octyl and adamantyl.

Halogenoalkyl on its own or as part of a radical in the general formulae contains 1 to 4, in particular 1 to 2, carbon atoms and preferably has 1 to 9, in particular 1 to 5, identical or different halogen atoms, preferably fluorine, chlorine or bromine, in particular fluorine and chlorine. Examples include trifluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-tert-butyl.

Optionally substituted alkoxy on its own or as part of a radical in the general formulae means straight-chain or branched alkoxy preferably having 1 to 6, in particular 1 to 4, carbon atoms. Examples include optionally substituted methoxy, ethoxy, n-propoxy, isopropoxy, n-butoxy, isobutoxy, sec-butoxy and tert-butoxy.

Optionally substituted alkoxyalkoxy on its own or as part of a radical in the general formulae means straight-chain or branched alkoxyalkoxy preferably having 1 to 6, in particular 1 to 4, carbon atoms. Examples include optionally substituted methoxymethoxy, methoxyethoxy, methoxy-n-propoxy and ethoxyisopropoxy.

Optionally substituted alkoxyalkoxyalkoxy on its own or as part of a radical in the general formulae means straight-chain or branched alkoxyalkoxyalkoxy preferably having 1 to 6, in particular 1 to 4, carbon atoms. Examples include optionally substituted methoxymethoxyethoxy, methoxy-ethoxyethoxy and methoxyethoxy-n-propoxy.

Optionally substituted halogenoalkoxy on its own or as part of a radical in the general formulae means straight-chain or branched halogenoalkoxy preferably having 1 to 6, in particular 1 to 4, carbon atoms. Examples include optionally substituted difluoromethoxy, trifluoromethoxy, trichloromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy and 2-chloro-1,1,2-trifluoroethoxy.

Optionally substituted alkylthio on its own or as part of a radical in the general formulae means straight-chain or branched alkylthio preferably having 1 to 6, in particular 1 to 4, carbon atoms. Examples include optionally substituted methylthio, ethylthio, n-propylthio, isopropylthio, n-butylthio, isobutylthio, sec-butylthio and tert-butylthio.

Optionally substituted halogenoalkylthio on its own or as part of a radical in the general formulae means straight-chain or branched halogenoalkylthio preferably having 1 to 6, in particular 1 to 4, carbon atoms. Examples include optionally substituted difluorometliylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio and 2-chloro-1,1,2-trifluoroethylthio.

Optionally substituted alkylcarbonyl on its own or as part of a radical in the general formulae means straight-chain or branched alkylcarbonyl preferably having 1 to 6, in particular 1 to 4, carbon atoms. Examples include optionally substituted methylcarbonyl, ethylcarbonyl, n-propylcarbonyl, isopropylcarbonyl, sec-butylcarbonyl and tert-butylcarbonyl.

Optionally substituted cycloalkylcarbonyl on its own or as part of a radical in the general formulae means mono-, bi- and tricyclic cycloalkylcarbonyl preferably having 3 to 10, in particular 3, 5 or 7, carbon atoms. Examples include optionally substituted cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptylcarbonyl, bicyclo[2.2.2]octylcarbonyl and adamantylcarbonyl.

Optionally substituted alkoxycarbonyl on its own or as part of a radical in the general formulae means straight-chain or branched alkoxy preferably having 1 to 6, in particular 1 to 4, carbon atoms. Examples include optionally substituted methoxycarbonyl, ethoxycarbonyl, n-propoxycarbonyl, isopropoxycarbonyl, n-butoxycarbonyl, isobutoxycarbonyl, sec-butoxycarbonyl and tert-butoxycarbonyl.

Aryl is, for example, a mono-, di- or polynuclear aromatic radical such as phenyl, naphthyl, tetrahydronaphthyl, indanyl, fluorenyl and the like, but preferably phenyl or naphthyl.

Optionally substituted aryl in the general formulae preferably means optionally substituted phenyl or naphthyl, in particular phenyl.

Optionally substituted arylalkyl in the general formulae preferably means arylalkyl which is optionally substituted in the aryl moiety and/or alkyl and preferably has 6 or 10, in particular 8, carbon atoms in the aryl moiety (preferably phenyl or naphthyl, in particular phenyl) and preferably 1 to 4, in particular 1 or 2, carbon atoms in the alkyl moiety, the alkyl moiety being straight-chain or branched. Preferred examples include optionally substituted benzyl and 1-phenylethyl.

The optionally substituted radicals of the general formulae may carry one or more, preferably 1 to 3, in particular 1 to 2, identical or different substituents. Examples of preferred substituents include:

Alkyl preferably having 1 to 4, in particular 1 to 2, carbon atoms, such as methyl, ethyl, n-propyl, isopropyl, n-butyl, isobutyl, sec-butyl and tert-butyl; alkoxy preferably having 1 to 4, in particular 1 to 2, carbon atoms, such as methoxy, ethoxy, n-propoxy, isopropoxy, n-butoxy, isobutoxy, sec-butoxy and tert-butoxy; alkylthio such as methylthio, ethylthio, n-propylthio, isopropylthio, n-butylthio, isobutylthio, sec-butylthio; halogenoalkyl preferably having 1 to 5, in particular 1 to 3, halogen atoms, where the halogen atoms are identical or different and are preferably fluorine, chlorine or bromine, in particular fluorine or chlorine, such as difluoromethyl, trifluoromethyl, trichloromethyl; hydroxyl; halogen, preferably fluorine, chlorine, bromine and iodine, in particular fluorine and chlorine; cyano; nitro; amino; monoalkyl- and dialkylamino preferably having 1 to 4, in particular 1 or 2, carbon atoms per alkyl group, such as methylamino, methylethylamino, dimethylamino, n-propylamino, isopropylamino, methyl-n-butylamino; alkylcarbonyl radicals such as methyl-carbonyl; alkoxycarbonyl preferably having 2 to 4, in particular 2 to 3, carbon atoms, such as methoxycarbonyl and ethoxycarbonyl; alkylsulfinyl having 1 to 4, in particular 1 to 2, carbon atoms; halogenoalkylsulfinyl having 1 to 4, in particular 1 to 2, carbon atoms and 1 to 5 halogen atoms, such as trifluoromethylsulfonyl; halogenoalkylsulfinyl having 1 to 4, in particular 1 to 2, carbon atoms and 1 to 5 halogen atoms, such as trifluoromethylsulfonyl, perfluoro-n-butylsulfonyl, perfluoroisobutylsulfonyl; arylsulfonyl preferably having 6 or 10 aryl carbon atoms, such as phenylsulfonyl; acyl, aryl, aryloxy which may in turn carry one of the abovementioned substituents, and the formimino radical (—HC=N—O-alkyl).

The number of these substituents is not limited, preference is given to 1 to 4 identical or different substituents. The presence of two identical or different substituents at the same atom or at atoms of cyclic amino groups is also possible.

Optionally substituted mono- or dialkylamino groups on their own or as part of a radical in the general formulae mean straight-chain or branched alkyl preferably having 1 to 6, in particular 1 to 4, carbon atoms. Examples of substituted mono- or dialkylamino groups include methylamino, ethylamino, dimethylamino, diethylamino, di-n-propylamino, diisopropylamino or dibutylamino.

Optionally substituted mono- or dialkoxyalkylamnino groups on their own or as part of a radical in the general formulae mean straight-chain or branched alkoxyalkyl preferably having 1 to 6, in particular 1 to 4, carbon atoms. Examples of substituted mono- or dialkoxyalkyl-amino groups include methoxymethylamino, methoxyethylamino, di-(methoxymethyl)-amino or di-(methoxyethyl)-amino.

Suitable cyclic amino groups include heteroaromatic or aliphatic ring systems having one or more nitrogen atoms as heteroatom, where the heterocycles may be saturated or unsaturated, comprise one ring system or more than one fused ring systems and optionally contain further heteroatoms such as, for example, one or two nitrogen, oxygen and sulfur, etc. Additionally, cyclic amino groups may also represent a spiral ring or a bridged ring system. The number of atoms forming cyclic amino groups is not limited, in the case of a one-ring system, for example, they comprise 3 to 8 atoms and in the case of a three-ring system 7 to 11 atoms.

Exanples of cyclic amino groups having saturated and unsaturated monocyclic groups with a nitrogen atom as heteroatom include 1-azetidinyl, pyrrolidino, 2-pyrrolin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl and homopiperidinyl; examples of cyclic amino groups having saturated and unsaturated monocyclic groups with two or more nitrogen atoms as heteroatoms include 1-imidazolidinyl, 1-imidazolyl, 1-pyrazolyl, 1-triazolyl, 1-tetrazolyl, 1-piperazinyl, 1-homopiperazinyl, 1,2-dihydro-pyridazin- 1-yl, 1,2-dihydropyrimidin- 1-yl, perhydropyrimidin-1-yl and 1,4-diazacyclo-heptan-1-yl; examples of cyclic amino groups having saturated and unsaturated monocyclic groups with one or two oxygen atoms and one to 3 nitrogen atoms as heteroatoms include oxazolidin-3-yl, 2,3-dihydroisoxazol-2-yl, isoxazol-2-yl, 1,2,3-oxadiazin-2-yl and morpholino, examples of cyclic amino groups having saturated and unsaturated monocyclic groups with one to three nitrogen atoms and one to two sulfuir atoms as heteroatoms include thiozolidin-3-yl, isothiazolin-2-yl, thiomorpholino, or dioxothiomorpholino; examples of cyclic amino groups having saturated and unsaturated fused cyclic groups include indol-1-yl, 1,2-dihydrobenzimidazol-1-yl and perhydropyrrolo[1,2-a]pyrazin-2-yl; examples of cyclic amino groups having spirocyclic groups include 2-azaspiro[4.5]decan-2-yl; examples of cyclic amino groups having bridged heterocyclic groups include 2-azabicyclo[2.2.1]heptan-7-yl.

Suitable amino protecting groups are acyl groups preferably having 1 to 6, in particular 1 to 4, carbon atoms, such as, for example, formyl, acetyl, propionyl, pivaloyl, hexanoyl or mono- (or di- or tri-)halogen-containing acyl groups, such as, for example, chloroacetyl, bromoacetyl, dichloroacetyl and trifluoroacetyl, alkoxycarbonyl groups preferably having 1 to 14, in particular 1 to 4, carbon atoms, such as, for example, methoxycarbonyl, ethoxycarbonyl, propoxycarbonyl, tert-butoxycarbonyl (Boc), tert-amyloxycarbonyl (Aoc), hexyloxycarbonyl, methylsulfonylethoxycarbonyl, adamantyloxycarbonyl (Adoc) and 1-[1-adamantyl]-1-methylethoxycarbonyl (Adpoc), carbamoyl groups, aroyl groups, such as, for example, phenylacetyl and phenylpropionyl, aryloxycarbonyl groups, such as, for example, phenoxycarbonyl and naphthyloxycarbonyl, aryloxyalkanoyl groups, such as, for example, phenoxyacetyl, and phenoxypropionyl, arylglyoxyloyl groups, such as, for example, phenylglyoxyloyl and naphthylglyoxyloyl, alkoxycarbonyl groups having conventional substituents, such as, for example, benzyloxycarbonyl (Cbo- or Cbz, Z), 4-methoxy-benzyloxycarbonyl, 3,5-dimethoxy-benzyloxycarbonyl, 4-phenylazo-benzyloxycarbonyl, phenethyloxycarbonyl, nitrobenzyloxycarbonyl, chlorobenzyloxycarbonyl, α,α-dimethyl-3,5-dimethoxy-benzyloxycarbonyl, 2-nitro-4,5-dimethoxybenzyloxycarbonyl (Nvoc), fluorenyl-9-methoxycarbonyl (Fmoc), substituted or unsubstituted alkylidene groups, such as, for example, benzylidene, hydroxybenzylidene, mono- (or di- or tri-)phenylalkyl-containing alkyl groups, such as, for example, benzyl, phenethyl, benzhydryl or triphenylmethyl (trityl), and the like.

Suitable hydroxyl protecting groups are optionally substituted alkyl groups preferably having 1 to 6, in particular 1 to 4, carbon atoms, such as, for example, tert-butyl, methylthiomethyl and trimethylsilyl, phenylalkyl-containing alkyl groups, such as, for example, benzyl or diphenylmethyl, heterocyclic groups, such as tetrahydropyranyl, and the like.

Suitable thiol protecting groups are optionally substituted alkyl groups preferably having 1 to 6, in particular 1 to 4, carbon atoms, such as, for example, acetamidomethyl and chloroacetamidomethyl, phenylalkyl-containing alkyl groups, such as, for example, benzyl, 4-methoxybenzyl, diphenylmethyl, triphenylmethyl and pyridyl-diphenylmethyl, and the like.

The further abovementioned protecting groups have the function, known in peptide chemistry, of protecting amino, hydroxyl or thiol groups of compounds temporarily.

Particular preference is given to compounds of the general formula (I) and salts thereof

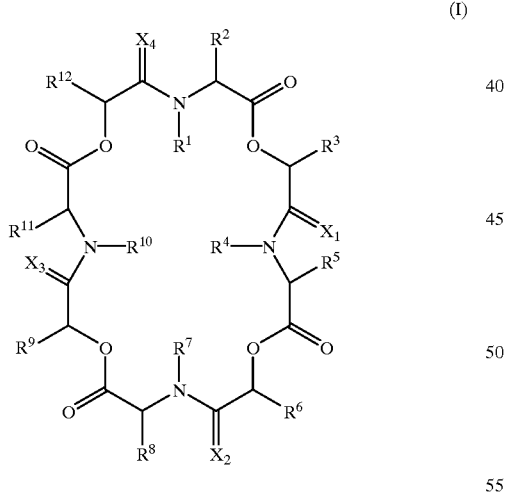

(I)

in which
$R^1$, $R^4$, $R^7$ and $R^{10}$ each represent $C_{1-4}$-alkyl, in particular methyl,
$R^2$, $R^5$, $R^8$ and $R^{11}$ each represent $C_{1-4}$-alkyl, in particular isobutyl,
$R^3$ and $R^9$ each represents $C_{1-4}$ alkyl, in particular methyl,
$R^6$ and $R^{12}$ each represent independently of one another $C_{1-4}$-alkyl, in particular methyl, hetaryl-$C_{1-2}$-alkyl, in particular benzothiazol-2-yl-methyl, alkoxycarbonylmethyl, in particular diphenylmethoxycarbonylmethyl, and optionally substituted benzyl, possible substituents including hydrogen, halogen, in particular bromine, fluorine, chlorine or iodine, cyano, carbamoyl, $C_{1-4}$-alkyl, in particular methyl, hydroxyl or hydroxyl carrying a protecting group, $C_{1-8}$-alkoxy, in particular methoxy, ethoxy, n-propyloxy, isopropyloxy, butyloxy, tert-butyloxy, octyloxy or triphenylmethoxy, $C_{1-4}$-alkoxy-$C_{1-4}$-alkoxy, in particular 2-methoxyethoxy, $C_{2-4}$-alkenyloxy, in particular allyloxy, hetaryl-$C_{1-4}$-alkoxy where the heterocycles again may carry substituents from the group consisting of $C_{1-4}$-alkyl, in particular methyl, isopropyl, sec-butyl and iso-butyl, $C_{3-6}$-cycloalkyl, in particular cyclopropyl and cyclohexyl, halogen, in particular chlorine, bromine, fluorine or iodine, in particular fur-2-yl-meth-oxy, fur-3-yl-methoxy, tetrahydrofur-2-yl-methoxy, N-boc-pyrrolidin-2-yl-methoxy, pyrrolidin-2-yl-methoxy, 5-sec-butyl- 1,2,4-oxadiazol-3-yl-pyridyl-methoxy, 5-cyclopropyl-1,2,4-oxadiazol-3-yl-methoxy, imidazol-5-yl-methoxy, thiazolyl-methoxy and tetrazol-5-yl-methoxy, nitro, anino or amino carrying a protecting group, amino-$C_{1-6}$-alkoxy or amino-$C_{1-6}$-alkoxy carrying a protecting group, in particular aminoethoxy, N-mono-$C_{1-6}$-alkylamino-$C_{1-6}$-alkoxy, in particular 2-N-methylamino-ethoxy, N,N-di-$C_{1-6}$-alkylamino-$C_{1-6}$-alkoxy, in particular N,N-diethyl-amino-methoxy, 2-N,N-dimethylamino-ethoxy or 2-N,N-diethylamino-ethoxy, N,N-Di-[($C_{1-6}$-alkoxy- $C_{1-6}$-alkyl)]amino $C_{1-6}$-alkoxy, in particular 2-[N,N-di(methoxyethyl)amino]-ethoxy, $C_{1-4}$-alkylamino, in particular N-methylamino, $C_{1-4}$-dialkylamino, in particular dimethylamino or diethylamino, $C_{3-7}$-cycloalkylamino- (which may contain one or more nitrogen atoms as ring-forming atoms and additionally oxygen or sulfur atoms) $C_{1-6}$-alkoxy, in particular 2-N-morpholino-ethoxy, 2-N-piperidino-ethoxy, pyrrolidinomethoxy, $C_{3-7}$-cyclo-alkylamino- (which may contain one or more nitrogen atoms as ring-formning atoms and additionally oxygen or sulfur atoms), in particular N-morpholino, N-thiomorpholino, piperidino, $C_{3-7}$-cyclo-alkylamino- (which may contain one or more nitrogen atoms as ring-forming atoms and additionally oxygen or sulfur atoms) sulfonyl, in particular N-morpholino-sulfonyl, n-thiomorpholino-sulfonyl, piperidinosulfonyl, N-($N^1$-methyl-piperazino)-sulfonyl, N-($N^1$-methoxy-carbonyl-piperazino)-sulfonyl, $N^1$-imidazolyl-sulfonyl, N,N-di [($C_{1-6}$alkoxy-$C_{1-6}$-alkyl)]amino-sulfonyl, in particular 2-[N,N-di(methoxy-ethyl)-aminol-sulfonyl, $C_{3-7}$-cyclo-al-kylamino- (which may contain one or more nitrogen atoms as ring-forming atoms and additionally oxygen or sulfur atoms)-$C_{1-6}$alkylaminosulfonyl, in particular 2-(N-morpholino)-ethylamino-sulfonyl, $C_{1-4}$-dialkylaminosulfonyl, in particular diethylaminosulfonyl, sulfamidyl, and (i)
$X^1$ represents sulfur,
$X^2$ $X^3$ and $X^4$ each represent independently of one another oxygen or sulfur, or (ii)
$X^2$ represents sulfur,
$X^1$, $X^3$ and $X^4$ each represent independently of one another oxygen or sulfur, or (iii)
$X^3$ represents sulfur,
$X^1$, $X^2$ and $X^4$ each represent independently of one another oxygen or sulfur, or (iv)
X⁴ represents sulfur,
X¹, X² and X³ each represent independently of one another oxygen or sulfur, and their optical isomers and racemates.

Very particular preference is given to compounds of the general formula (I) and salts thereof $$\text{(I)}$$

[Structure of cyclic compound with substituents $R^1$ through $R^{12}$ and $X_1$ through $X_4$]

in which
(a) $R^1$, $R^4$, $R^7$ and $R^{10}$ each represent methyl,
$R^2$, $R^5$, $R^8$ and $R^{11}$ each represent isobutyl,
$R^3$ and $R^9$ each represent methyl,
$R^6$ represents unsubstituted benzyl,
$R^{12}$ represents substituted benzyl,
possible substituents in the para position of the phenyl ring including hydrogen, $C_{1-8}$-alkoxy, in particular methoxy, tert-butyloxy, hetaryl-$C_{1-4}$-alkoxy, in particular fur-2-yl-methoxy, tetrahydrofiur-2-yl-methoxy, N-boc-pyrrolidin-2-yl-methoxy, pyrid-2-yl-methoxy, pyrrolidin-2-yl-methoxy, 5-sec-butyl-1,2,4-oxadiazol-3-yl-methoxy, 5-cyclopropyl-1,2,4-oxadiazol-3-yl-methoxy, imidazol-5-yl-methoxy, nitro, amino, N,N-di-$C_{1-6}$-alkylamino-$C_{1-6}$-alkoxy, in particular N,N-diethylamino-methoxy or 2-N,N-diethylamino]-ethoxy, N,N-di-[($C_{1-6}$-alkoxy-$C_{1-6}$-alkyl)]amino-$C_{1-6}$-alkoxy, in particular 2-[N,N-di(methoxyethyl)amino]-ethoxy, $C_{1-4}$-dialkylamino, in particular dimethylamino, $C_{3-7}$-cycloalkylamino- (which may contain one or more nitrogen atoms as ring-forming atoms and additionally oxygen or sulfur atoms) -$C_{1-6}$-alkoxy, in particular 2-N-morpholino-ethoxy, $C_{3-7}$-cyclo-alkylamino- (which may contain one or more nitrogen atoms as ring-forming atoms and additionally oxygen or sulfur atoms)-sulfonyl, in particular N-morpholino-sulfonyl, piperidinosulfonyl, N-($N^1$-methoxycarbonyl-piperazino)-sulfonyl, N,N-di-[($C_{1-6}$alkoxy-$C_{1-6}$-alkyl)]amino-sulfonyl, in particular 2-[N,N-di(methoxyethyl)amino]-sulfonyl, $C_{1-4}$-dialkylamino-sulfonyl, in particular diethylaminosulfonyl, and (i)
X¹ represents sulfur,
X², X³ and X⁴ each represent independently of one another oxygen or sulfur, or
(ii)
X² represents sulfur,
X¹, X³ and X⁴ each represent independently of one another oxygen or sulfur, or
(iii)
X³ represents sulfur,
X¹, X² and X⁴ each represent independently of one another oxygen or sulfur, or
(iv)
X⁴ represents sulfur,
X¹, X² and X³ each represent independently of one another oxygen or sulfur, or (b) $R^1$, $R^4$, $R^7$ and $R^{10}$ each represent methyl,
$R^2$, $R^5$, $R^8$ and $R^{11}$ each represent isobutyl,
$R^3$ and $R^9$ each represent methyl,
$R^6$ and $R^{12}$ each represent identically substituted benzyl,
possible substituents in the para position of the phenyl ring including hydrogen, $C_{1-8}$-alkoxy, in particular methoxy, tert-butyloxy, hetaryl-$C_{1-4}$-alkoxy, in particular fur-2-yl-methoxy, tetrahydrofur-2-yl-methoxy, N-boc-pyrrolidin-2-yl-methoxy, pyrid-2-yl-methoxy, pyrrolidin-2-yl-methoxy, 5-sec-butyl-1,2,4-oxadiazol-3-yl-methoxy, 5-cyclopropyl-1,2,4-oxadiazol-3-yl-methoxy, imidazol-5-yl-methoxy, nitro, amino, N,N-di-$C_{1-6}$-alkylamino-$C_{1-6}$-alkoxy, in particular N,N-diethylamino-methoxy or 2-N,N-diethylamino-ethoxy, N,N-di-[($C_{1-6}$-alkoxy-$C_{1-6}$-alkyl)]amino-$C_{1-6}$-alkoxy, in particular 2-[N,N-di(methoxyethyl)amino]-ethoxy, $C_{1-4}$-dialkylamino, in particular dimethylamino, $C_{3-7}$-cycloalkylamino- (which may contain one or more nitrogen atoms as ring-forming atoms and additionally oxygen or sulfur atoms) -$C_{1-6}$-alkoxy, in particular 2-N-morpholino-ethoxy, $C_{3-7}$-cyclo-alkylarnino- (which may contain one or more nitrogen atoms as ring-forming atoms and additionally oxygen or sulfur atoms), in particular N-morpholino, N-thiomorpholino, piperidino, $C_{3-7}$-cycloalkylamino- (which may contain one or more nitrogen atoms as ring-forming atoms and additionally oxygen or sulfur atoms)-sulfonyl, in particular N-morpholino-sulfonyl, piperidinosulfonyl, N-($N^1$-methoxycarbonyl-piperazino)-sulfonyl, N,N-di-[($C_{1-6}$-alkoxy-$C_{1-6}$-alkyl)]amino-sulfonyl, in particular 2-[N,N-di(methoxyethyl)amino]-sulfonyl, $C_{1-4}$-dialkylamino-sulfonyl, in particular diethylaminosulfonyl, and (i) X¹ represents sulfur,
X², X³ and X⁴ each represent independently of one another oxygen or sulfur, or
(ii)
X² represents sulfur,
X¹, X³ and X⁴ each represent independently of one another oxygen or sulfur, or
(iii)
X³ represents sulfur,
X¹, X² and X⁴ each represent independently of one another oxygen or sulfur, or
(iv)
X⁴ represents sulfur,
X¹, X² and X³ each represent independently of one another oxygen or sulfur, and their optical isomers and racemates.

Most particularly preferred are compounds of the general formula (I) and salts thereof

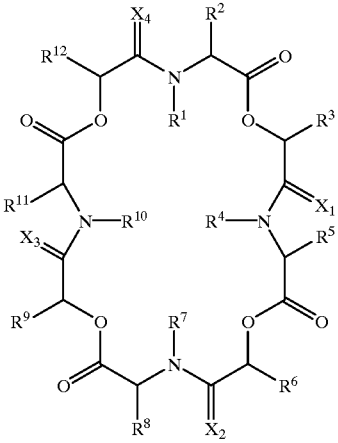

(I)

in which
(a) $R^1$, $R^4$, $R^7$ and $R^{10}$ each represent methyl,
$R^2$, $R^5$, $R^8$ and $R^{11}$ each represent isobutyl,
$R^3$ and $R^9$ each represent methyl,
$R^6$ represents unsubstituted benzyl,
$R^{12}$ represents substituted benzyl,
possible substituents in the para position of the phenyl ring including hydrogen, $C_{1-8}$-alkoxy, in particular tert-butyloxy, hetaryl-$C_{1-4}$-alkoxy, in particular fur-2-yl-meth-oxy, tetrahydrofur-2-yl-methoxy, N-boc-pyrrolidin-2-yl-methoxy, pyrid-2-yl-methoxy, pyrrolidin-2-yl-methoxy, 5-sec-butyl-1,2,4-oxadiazol-3-yl-methoxy, nitro, amino, N,N-di-$C_{1-6}$-alkylamino-$C_{1-6}$-alkoxy, in particular 2-N,N-diethylamino-ethoxy, N,N-di-[($C_{1-6}$-alkoxy-$C_{1-6}$-alkyl)]amino-$C_{1-6}$-alkoxy, in particular 2-[N,N-di(methoxyethyl)amino]-ethoxy, $C_{1-4}$-dialkylamino, in particular dimethylamino, $C_{3-7}$-cyclo-alkylamino- (which may contain one or more nitrogen atoms as ring-forming atoms and additionally oxygen or sulfur atoms) -$C_{1-6}$-alkoxy, in particular 2-N-morpholino-ethoxy, $C_{3-7}$-cycloalkylamino- (which may contain one or more nitrogen atoms as ring-forming atoms and additionally oxygen or sulfur atoms), in particular N-morpholino, and
(i)
$X^1$ represents sulfur,
$X^2$, $X^3$ and $X^4$ each represent independently of one another oxygen or sulfur, or
(ii)
$X^2$ represents sulfur,
$X^1$, $X^3$ and $X^4$ each represent independently of one another oxygen or sulfur, or
(iii)
$X^3$ represents sulfur,
$X^1$, $X^2$ and $X^4$ each represent independently of one another oxygen or sulfur, or
(iv)
$X^4$ represents sulfur,
$X^1$, $X^2$ and $X^3$ each represent independently of one another oxygen or sulfur, or
(b) $R^1$, $R^4$, $R^7$ and $R^{10}$ each represent methyl,
$R^2$, $R^5$, $R^8$ and $R^{11}$ each represent isobutyl,
$R^3$ and $R^9$ each represent methyl,
$R^6$ and $R^{12}$ each represent identically substituted benzyl,
possible substituents in the para position of the phenyl ring including hydrogen, $C_{1-8}$-alkoxy, in particular tert-butyloxy, hetaryl-$C_{1-4}$-alkoxy, in particular fur-2-yl-methoxy, tetrahydrofur-2-yl-methoxy, N-boc-pyrrolidin-2-yl-methoxy, pyrid-2-yl-methoxy, pyrrolidin-2-yl-methoxy, 5-sec-butyl-1,2,4-oxadiazol-3-yl-methoxy, nitro, amino, N,N-di-$C_{1-6}$-alkylamino-$C_{1-6}$-alkoxy, in particular 2-N,N-diethylaminoethoxy, N,N-di-[($C_{1-6}$-alkoxy-$C_{1-6}$-alkyl)]amino-$C_{1-6}$-alkoxy, in particular 2-[N,N-di(methoxyethyl)amino]-ethoxy, $C_{1-4}$-dialkylamino, in particular dimethylamino, $C_{3-7}$-cyclo-alkylamino- (which may contain one or more nitrogen atoms as ring-forming atoms and additionally oxygen or sulfur atoms) -$C_{1-4}$-alkoxy, in particular 2-N-morpholino-ethoxy, $C_{3-7}$-cyclo-alkylamino- (which may contain one or more nitrogen atoms as ring-forming atoms and additionally oxygen or sulfur atoms), in particular N-morpholino, and
(i)
$X^1$ represents sulfur,
$X^2$, $X^3$ and $X^4$ each represent independently of one another oxygen or sulfur, or
(ii)
$X^2$ represents sulfur,
$X^1$, $X^3$ and $X^4$ each represent independently of one another oxygen or sulfur, or
(iii)
$X^3$ represents sulfur,
$X^1$, $X^2$ and $X^4$ each represent independently of one another oxygen or sulfur, or
(iv)
$X^4$ represents sulfur,
$X^1$, $X^2$ and $X^3$ each represent independently of one another oxygen or sulfur.

The thiodepsipeptides of the general formula (I) and salts thereof to be used according to the invention additionally contain one or more chiral centers and may thus be present as pure stereoisomers or in the form of various mixtures of enantiomers and diastereomers which, if required, may be separated in a conventional manner or else may be prepared by stereoselective reactions in combination with the use of stereo-chemically pure starting materials.

However, preference is given to employing the optically active stereoisomeric forms of the compounds of the general formula (I) and salts thereof according to the invention. Particularly preferably, those cyclic depsipeptides are used which are composed of amino acids of the (S) configuration (L form) and of hydroxycarboxylic acids of the (R) configuration (D form) as ring building blocks.

The invention therefore provides the pure enantiomers and diastereomers and also mixtures thereof for controlling endoparasites, in particular in the fields of medicine and veterinary medicine.

Suitable salts of the thiodepsipeptides of the general formula (I) in clude conventional non-toxic salts, i.e. salts with various bases and salts with added acids. Preference is given to salts with inorganic bases, such as alkali metal salts, for example sodium salts potassium salts or cesium salts, alkaline earth metal salts, for example calcium salts or magnesium salts, ammonium salts, salts with organic bases and with inorganic amines, for e xample triethylammoniuc s alts, dicyclohexylammonium salts, N,N'-dibenzlethylenediammonium salts, pyridinium salts, picolinium salts or ethanolantonium salts, salts with inorganic acids, for example hydrochlorides, hydrobromides, dihydrosulfates, trihydrosulfates, or phosphates, salts with organic carboxylic acids or organic sulfonic acids, for example formates, acetates, trifluoroacetates, maleates, tartrates, methanesulfonates, benzenesulfonates or paratoluenesulfonates, salts with basic amino acids, for example arginates, aspartates or glutamates, and the like.

Specifically, mention may be made of the following cyclodepsipeptides having 24 ring atoms:

cyclo(-N-methyl-L-leucyl-D-thiolactyl-N-methyl-L-leucyl-D-phenylthiolactyl-N-methyl-L-leucyl-D-thiolactyl-N-methyl-L-leucyl-D-phenylthiolactyl-N-), cyclo(-N-methyl-L-leucyl-D-lactyl-N-methyl-L-leucyl-D-phenylthiolactyl-N-methyl-L-leucyl-D-thiolactyl-N-methyl-L-leucyl-D-phenythiolactyl-), cyclo(-N-methyl-L-leucyl-D-thiolactyl-N-methyl-L-leucyl-D-phenylthiolactyl-N-methyl-L-leucyl-D-thiolactyl-N-methyl-L-leucyl-D-phenyllactyl-), cyclo(-N-methyl-L-leucyl-D-thiolactyl-N-methyl-L-leucyl-D-phenylthiolactyl-N-methyl-L-leucyl-D-lactyl-N-mehtyl-L-leucyl-D-phenyllactyl-), cyclo(-N-methyl-L-leucyl-D-lactyl-N-methyl-L-leucyl-D-phenylthiolactyl-N-methyl-L-leucyl-D-thiolactyl-N-methyl-L-leucyl-D-phenyllactyl-), cyclo(-N-methyl-L-leucyl-D-thiolactyl-N-methyl-L-leucyl-D-phenyllactyl-N-methyl-L-leucyl-D-thiolactyl-N-methyl-L-leucyl-D-phenyllactyl-), cyclo(-N-methyl-L-leucyl-D-lactyl-N-methyl-L-leucyl-D-phenylthiolactyl-N-methyl-L-leucyl-D-lactyl-N-methyl-L-leucyl-D-phenylthiolactyl-), cyclo(-N -methyl-L-leucyl-D-thiolactyl-N-methyl-L-leucyl-D-phenyllactyl-N-methyl-L-leucyl-D-lactyl-N-methyl-L-leucyl-D-phenyllactyl-), cyclo(-N-methyl-L-leucyl-D-lactyl-N-methyl-L-leucyl-D-phenylthiolactyl-N-methyl-L-leucyl-D-lactyl-N-methyl-L-leucyl-D-phenyllactyl-), cyclo(-N-methyl-L-leucyl-D-thiolactyl-N-methyl-L-leucyl-D-4-nitro-phenylthiolactyl-N-methyl-L-leucyl-D-thiolactyl-N-methyl-L-leucyl-D-4-nitro-phenylthiolactyl-), cyclo(-N -methyl-L-leucyl-D-thiolactyl-N-methyl-L-leucyl-D4-nitro-phenylactyl-N-methyl-L-leucyl-D-lactyl-N-methyl-L-leucyl-D-4-nitro-phenyllactyl-), cyclo(-N-methyl-L-leucyl-D-thiolactyl-N-methyl-L-leucyl-D-4-tert-butyloxyphenythiolactyl-N-methyl-L-leucyl-D-thiolactyl-N-methyl-L-leucyl-D-4-tert-butyloxyphenylthiolactyl-), cyclo(-N-methyl-L-leucyl-D-thiolactyl-N-methyl-L-leucyl-D-4-tert-butyloxyphenyllactyl-N-methyl-L-leucyl-D-lactyl-N-methyl-L-leucyl-D-4-tert-butyloxyphenyllactyl-), cyclo(-N-methyl-L-leucyl-D-thiolactyl-N-methyl-L-leucyl-D4-N-morpholinophenylthiolactyl-N-methyl-L-leucyl-D-thiolactyl-N-methyl-L-leucyl-D-4-N-morpholino-phenylthiolactyl-), cyclo(-N-methyl-L-leucyl-D-lactyl-N-methyl-L-leucyl-D-4-N-morpholino-phenylthiolactyl-N-methyl-L-teucyl-D-thiolactyl-N-methyl-L-leucyl-D-4-N-morpholino-phenylthiolactyl-), cyclo(-N-methyl-L-leucyl-D-thiolactyl-N-methyl-L-leucyl-D-4-N-morpholinophenylthiolactyl-N-methyl-L-leucyl-D-thiolactyl-N-methyl-L-leucyl-D-4-N-morpholinophenyllactyl-), cyclo(-N-methyl-L-leucyl-D-thiolactyl-N-methyl-L-leucyl-D-4-N-morpholinophenylthiolactyl-N-methyl-L-leucyl-D-lactyl-N-methyl-L-leucyl-D-4-N-morpholino-phenyllactyl-), cyclo(-N-methyl-L-leucyl-D-lactyl-N-methyl-L-leucyl-D-4-N-morpholinophenylthiolactyl-N-methyl-L-leucyl-D-thiolactyl-N-methyl-L-leucyl-D-4-N-morpholinophenyllactyl-), cyclo(-N-methyl-L-leucyl-D-thiolactyl-N-methyl-L-leucyl-D-4-N-morpholinophenyllactyl-N-methyl-L-leucyl-D-thiolactyl-N-methyl-L-leucyl-D-4-N-morpholinophenyllactyl-), cyclo(-N-methyl-L-leucyl-D-lactyl-N-methyl-L-leucyl-D-4-N-morpholinophenylthiolactyl-N-methyl-L-leucyl-D-lactyl-N-methyl-L-leucyl-D-4-N-morpholinophenylthiolactyl-), cyclo(-N-methyl-L-leucyl-D-thiolactyl-N-methyl-L-leucyl-D-4-N-morpholinophenyllactyl-N-methyl-L-leucyl-D-lactyl-N-methyl-L-leucyl-D-4-N-morpholinophenyllactyl-), cyclo(-N-methyl-L-leucyl-D-lactyl-N-methyl-L-leucyl-D-4-N-morpholinophenylthiolactyl-N-methyl-L-leucyl-D-lactyl-N-methyl-L-leucyl-D4-N-morpholinophenyllactyl-), cyclo[-N-methyl-L-leucyl-D-thiolactyl-N-methyl-L-leucyl-D-4-(fur-2-y 1-methoxy)-phenylthiolactyl-N-methyl-L-leucyl-D-thiolactyl-N-methyl-L-leucyl-D-4-(fur-2-yl-methoxy)-phenylthiolactyl-], cyclo[-N-methyl-L-leucyl-D-thiolactyl-N-methyl-L-leucyl-D4-(fur-2-yl-methoxy)-phenyllactyl-N-methyl-L-leucyl-D-thiolactyl-N-methyl-L-leucyl-D-4-(fur-2-yl-methoxy)-phenyllactyl-], cyclo[-N-methyl-L-leucyl-D-thiolactyl-N-methyl-L-leucyl-D4-(fur-2-yl-methoxy)-phenyllactyl-N-methyl-L-leucyl-D-lactyl-N-methyl-L-leucyl-D-4-(fur-2-yl-methoxy)-phenyllactyl-], cyclo[-N-methyl-L-leucyl-D-thiolactyl-N-methyl-L-leucyl-D-4-(fur-2-yl-methoxy)-phenylthiolactyl-N-methyl-L-leucyl-D-thiolactyl-N-methyl-L-leucyl-D-phenylthiolactyl-], cyclo[-N-methyl-L-leucyl-D-thiolactyl-N-methyl-L-leucyl-D-4-(fur-2-yl-methoxy)-phenyllactyl-N-methyl-L-leucyl-D-thiolactyl-N-methyl-L-teucyl-D-phenyllactyl-], cyclo[-N-methyl-L-leucyl-D-thiolactyl-N-methyl-L-leucyl-D-4-(fur-2-yl-methoxy)-phenyllactyl-N-methyl-L-leucyl-D-lactyl-N-methyl-L-leucyl-D-phenyllactyl-], cyclo[-N-methyl-L-leucyl-D-lactyl-N-methyl-L-leucyl-D-4-(fur-2-yl-methoxy)-phenyllactyl-N-methyl-L-leucyl-D-thiolactyl-N-methyl-L-leucyl-D-phenyllactyl-], cyclo(-N-methyl-L-leucyl-D-thiolactyl-N-methyl-L-leucyl-D-4-(tetrahydrofur-2-yl-metloxy)-phenylthiolactyl-N-methyl-L-leucyl-D-thiolactyl-N-methyl-L-leucyl-D-4-N-(tetrahydrofur-2-yl-methoxy)-phenylthiolactyl-], cyclo[-N-methyl-L-leucyl-D-thiolactyl-N-methyl-L-leucyl-D4-(tetrahydrofur-2-yl-methoxy)-phenyllactyl-N-methyl-L-leucyl-D-thiolactyl-N-methyl-L-leucyl-D4-(tetrahydrofur-2-yl-methoxy)-phenyllactyl-], cyclo[-N-methyl-L-leucyl-D-thiolactyl-N-methyl-L-leucyl-D-4-(tetrahydrofulr-2-yl-methoxy)-phenyllactyl-N-methyl-L-leucyl-D-lactyl-N-methyl-L-leucyl-D-4-(tetrahydrofur-2-yl-methoxy)-phenyllactyl-], cyclo[-N-methyl-L-leucyl-D-thiolactyl-N-methyl-L-leucyl-D-4-(pyrrolidin-2-yl-methoxy)-phenyl-thiolactyl-N-methyl-L-leucyl-D-thiolactyl-N-methyl-L-leucyl-D-4-(pyrrolidin-2-yl-methoxy)-phenylthiolactyl-], cyclo(-N-methyl-L-leucyl-D-thiolactyl-N-methyl-L-leucyl-D-4-(pyrrolidin-2-yl-methoxy)-phenyllactyl-N-methyl-L-leucyl-D-thiolactyl-N-methyl-L-leucyl-D-4-(pyrrolidin-2-yl-methoxy)-phenyllactyl-], cyclo[-N-methyl-L-leucyl-D-thiolactyl-N-methyl-L-leucyl-D-4-(pyrrolidin-2-yl-methoxy)-phenyllactyl-N-methyl-L-leucyl-D-lactyl-N-methyl-L-leucyl-D-4-(pyrrolidin-2-yl-methoxy)-phenyllactyl-], cyclo[-N-methyl-L-leucyl-D-thiolactyl-N-methyl-L-leucyl-D-4-(pyrrolidin-2-yl-methoxy3-phenylthiolactyl-N-methyl-L-leucyl-D-thiolactyl-N-methyl-L-leucyl-D-phenylthiolactyl-), cyclo[-N-methyl-L-leucyl-D-thiolactyl-N-methyl-L-leucyl-D-4-(pyrrolidin-2-yl-methoxy)-phenyllactyl-N-methyl-L-leucyl-D-thiolactyl-N-methyl-L-leucyl-D-phenyllactyl-], cylo[-N-methyl-L-leucyl-D-thiolactyl-N-methyl-L-leucyl-D-4-(pyrrolidin-2-yl-methoxy)-phenyllactlyl-N-methyl-L-leucyl-D-thiolactyl-N-methyl-L-leucyl-D-phenyllactyl-], cyclo[-N-methyl-L-leucyl-D-lactyl-N-methyl-L-leucyl-D-4-(pyrrolidin-2-yl-methoxy)-phenyllactyl-N-methyl-L-leucyl-D-thiolactyl-N-methyl-L-leucyl-D-phenyllactyl-], cyclo[-N-methyl-L-leucyl-D-thiolactyl-N-methyl-L-leucyl-D4-(5-sec-butyl-1,2,4-oxadiazol-3-yl-methoxy)-phenylthiolactyl-N-methyl-L-leucyl-D-thiolactyl-N-methyl-L-leucyl-D-4-(5-sec-butyl-1,2,4-oxadiazol-3-yl-methoxy)-phenylthiolactyl-], cyclo[-N-methyl-L-leucyl-D-thiolactyl-N-methyl-L-leucyl-D-4-(5-sec-butyl-1,2,4-oxadiazol-3-yl-methoxy)-phenyllactyl-N-methyl-L-leucyl-D-thiolactyl-N-methyl-L-leucyl-D-4-(5-sec-butyl-1,2,4-oxadiazol-3-yl-metboxy)-phenyllactyl-], cyclo[-N-methyl-L-leucyl-D-thiolactyl-N-methyl-L-leucyl-D-4-(5-sec-butyl-1,2,4-oxadiazol-3-yl-methoxy)-phenyllactyl-N-methyl-L-leucyl-D-lactyl-N-methyl-L-leucyl-D-4-(5-sec-butyl-1,2,4-oxadiazol-3-yl-methoxy)-phenyllactyl-], cyclo[-N-methyl-L-leucyl-D-thiolactyl-N-methyl-L-leucyl-D-4-(5-sec-butyl-1,2,4-oxadiazol-3-yl-methoxy)-phenylthiolactyl-N-methyl-L-leucyl-D-thiolactyl-N-methyl-L-leucyl-D-phenylthiolactyl-], cyclo[-N-methyl-Leucyl-D-thiolactyl-N-methyl-L-leucyl-D-4-(cyclopropyl-1,2,4-oxadiazol-3-yl-methoxy)-phenylthiolactyl-N-methyl-L-leucyl-D-thiolactyl-N-methyl-L-leucyl-D-phenylthiolactyl-], cyclo[-N-methyl-L-leucyl-D-thiolactyl-N-methyl-L-leucyl-D-4-(tetra-5-yl-methoxy)-phenylthiolactyl-N-methyl-L-leucyl-D-thiolactyl-N-methyl-L-leucyl-D-phenyl-thiolactyl-], cyclo[-N-methyl-L-leucyl-D-thiolactyl-N-methyl-L-leucyl-D-4-(2-N,N-diethylaminoethoxy)-phenylthiolactyl-N-methyl-L-leucyl-D-thiolactyl-N-methyl-L-leucyl-D-phenylthiolactyl-], cyclo[-N-methyl-L-leucyl-D-thiolactyl-N-methyl-L-leucyl-D-4-(2-N,N-diethylaminoethoxy)-phenylthiolactyl-N-methyl-L-leucyl-D-thiolactyl-N-methyl-L-leucyl-D-4-(2-N,N-diethylamino-ethoxy)-phenylthiolactyl-], cyclo[-N-methyl-L-leucyl-D-thiolactyl-N-methyl-L-leucyl-D-4-(2-N,N-diethylaminoethoxy)-phenyllactyl-N-methyl-L-leucyl-D-thiolactyl-N-methyl-L-leucyl-D-4-(2-N,N-dietbylaminoethoxy)-phenyllactyl-], cyclo[-N-methyl-L-leucyl-D-thiolactyl-N-methyl-L-leucyl-D-4-(2-N,N-diethylaminoethoxy)-phenyllactyl-N-methyl-L-leucyl-D-lactyl-N-methyl-L-leucyl-D-4-(2-N,N-diethylaminoethoxy)-phenyllactyl-], cyclo[-N-methyl-L-leucyl-D-thiolactyl-N-methyl-L-leucyl-D-4-(N,N-diethylamninomethoxy)-phenylthiolactyl-N-methyl-L-leucyl-D-thiolactyl-N-methyl-L-leucyl-D4-(N,N-diethylaminomethoxy)-phenylthiolactyl-], cyclo[-N-methyl-L-leucyl-D-thiolactyl-N-methyl-L-leucyl-D-4-(N,N-diethylaminomethoxy)-phenyllactyl-N-methyl-L-leucyl-D-thiolactyl-N-methyl-L-leucyl-D-4-(N,N-diethylaminomethoxy)-phenyllactyl-], cyclo[-N-methyl-L-leucyl-D-thiolactyl-N-methyl-L-leucyl-D-4-(N,N-diethylaminomethoxy)-phenyllactyl-N-methyl-L-leucyl-D-lactyl-N-methyl-L-leucyl-D-4 (N,N-diethylaminomethoxy)-phenyllactyl-], cyclo[-N-methyl-L-leucyl-D-thiolactyl-N-methyl-L-leucyl-D-4-(2-N-morpholinoethoxy)-phenylthiolactyl-N-methyl-L-leucyl-D-thiolactyl-N-methyl-L-leucyl-D-4-(2-N-morpholinoethoxy)-phenylthiolactyl-], cyclo[-N-methyl-L-leucyl-D-thiolactyl-N-methyl-L-leucyl-D-4-(2-N-morpholinoethoxy)-phenyllactyl-N-methyl-L-leucyl-D-lactyl-N-methyl-L-leucyl-D-4-(2-N-morpholinoethoxy)-phenyllactyl-], cyclo[-N-methyl-L-leucyl-D-thiolactyl-N-methyl-L-leucyl-D-4-(N,N-dimethoxyethylaminoethoxy)-phenylthiolactyl-N-methyl-L-leucyl-D-thiolactyl-N-methyl-L-leucyl-D-4-(N,N-dimethoxyethylaminoethoxy)-phenylthiolactyl-], cyclo[-N-methyl-L-leucyl-D-thiolactyl-N-methyl-L-leucyl-D-4-(N,N-dimethoxyethylaminoethoxy)-phenylthiolactyl-N-methyl-L-leucyl-D-thiolactyl-N-methyl-L-leucyl-D-phenylthiolactyl-], cyclo[-N-methyl-L-leucyl-D-thiolactyl-N-methyl-L-leucyl-D-4-(N-piperidino-sulfonyl)-phenylthiolactyl-N-methyl-L-leucyl-D-thiolactyl-N-methyl-L-leucyl-D4-(N-piperidinosulfonyl)-phenylthiolactyl-], cyclo[-N-methyl-L-leucyl-D-thiolactyl-N-methyl-L-leucyl-D-4-(N-piperidino-sulfonyl)-phenyllactyl-N-methyl-L-leucyl-D-lactyl-N-methyl-L-leucyl-D-4(N-piperidinosulfonyl)-phenyllactyl-], cyclo[-N-methyl-L-leucyl-D-thiolactyl-N-methyl-L-leucyl-D-4-(N-morpholinomethoxy)-phenylthiolactyl-N-methyl-L-leucyl-D-thiolactyl-N-methyl-L-leucyl-D-phenylthiolactyl-], cyclo[-N-methyl-L-leucyl-D-thiolactyl-N-methyl-L-leucyl-D-4-(N-morpholinomethoxy)-phenyllactyl-N-methyl-L-leucyl-D-lactyl-N-methyl-L-leucyl-D-phenyllactyl-], cyclo[-N-metyl-L-leucyl-D-thiolactyl-N-methyl-L-leucyl-D-4-(N,N-diethylaminomethoxy)-phenylthiolactyl-N-methyl-L-leucyl-D-thiolactyl-N-methyl-L-leucyl-D-phenylthiolactyl-], cyclol-N-methyl-L-leucyl-D-thiolactyl-N-methyl-L-leucyl-D-4-(N,N-diethylaminomethoxy)-phenyllactyl-N-methyl-L-leucyl-D-lactyl-N-methyl-L-leucyl-D-phenyllactyl-], cyclo[-N-methyl-L-leucyl-D-thiolactyl-N-methyl-L-leucyl-D-4-(pyrid-2-yl-methoxy)-phenylthiolactyl-N-methyl-L-leucyl-D-thiolactyl-N-methyl-L-leucyl-D-4-(pyrid-2-yl-methoxy)-phenylthiolactyl-], cyclo[-N-methyl-L-leucyl-D-thiolactyl-N-methyl-L-leucyl-D-4-(pyrid-2-yl-methoxy)-phenyllactyl-N-methyl-L-leucyl-D-lactyl-N-methyl-L-leucyl-D-4-(pyrid-2-yl-methoxy)-phenyllactyl-], cyclo[-N-methyl-L-leucyl-D-thiolactyl-N-methyl-L-
leucyl-D4-(pyrid-2-yl-methoxy)-phenyllactyl-N-
methyl-L-leucyl-D-thiolactyl-N-methyl-L-leucyl-D-4-
(pyrid-2-yl-methoxy)-phenyllactyl-], The compounds of the general formula (I) are novel, they can be prepared for example by the abovementioned process.

Surprisingly, the novel thiodepsipeptides of the general formula (I) can be obtained from the corresponding depsipeptides of the general formula (II) by thionation of one or more amide groups.

Below, the process according to the invention is illustrated by selected examples (see also the preparation examples).

If, for example, in process 2 the cyclic depsipeptide cyclo(-N-methyl-L-leucyl-D-lactyl-N-methyl-L-leucyl-D-phenyllactyl-N-methyl-L-leucyl-D-lactyl-N-methyl-L-leucyl-D-phenyllactyl-) (PF 1022A) is used as compound of the general formula (II) for thionation and "Lawesson's Reagent" is used as thionizing agent, cyclo(-N-methyl-L-leucyl-D-thiolactyl-N-methyl-L-leucyl-D-phenylthiolactyl-N-methyl-L-leucyl-D-thiolactyl-N-methyl-L-leucyl-D-phenylthiolactyl-) (cf. scheme I) is formed.

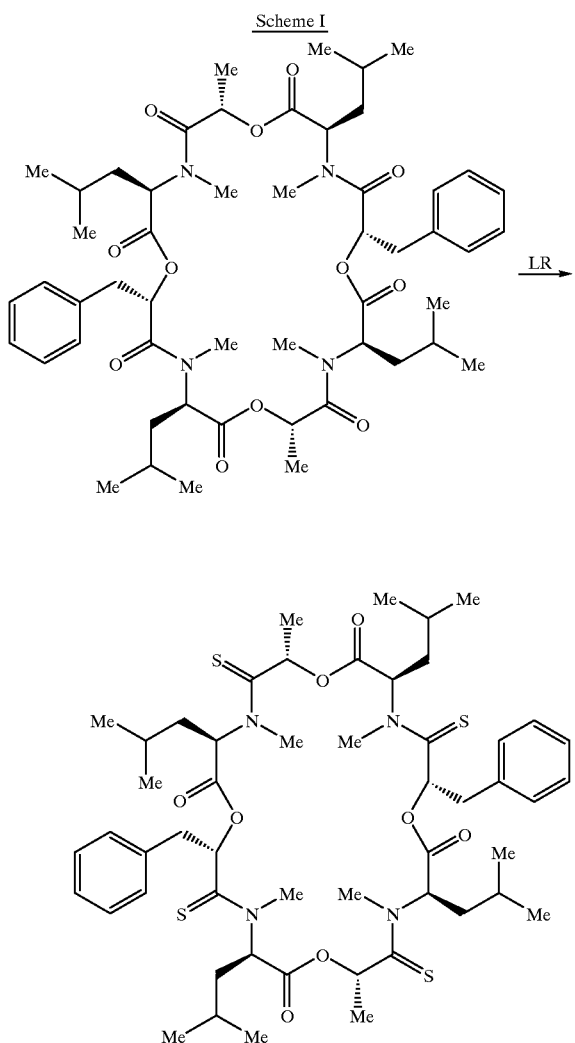

LR: Lawesson's Reagent

If, in a further embodiment of process 2, the cyclic depsipeptide cyclo(-N-methyl-L-leucyl-D-lactyl-N-methyl-L-leucyl-D-phenyllactyl-N-methyl-L-leucyl-D-lactyl-N-methyl-L-leucyl-D-phenyllactyl-) (PF 1022A) is used as compound of the general formula (II) and "Belleau's Reagent" is used as thionizing agent, cyclo(-N-methyl-L-leucyl-D-thiolactyl-N-methyl-L-leucyl-D-phenyllactyl-N-methyl-L-leucyl-D-lactyl-N-methyl-L-leucyl-D-phenyllactyl-) (cf. scheme II) is formed selectively.

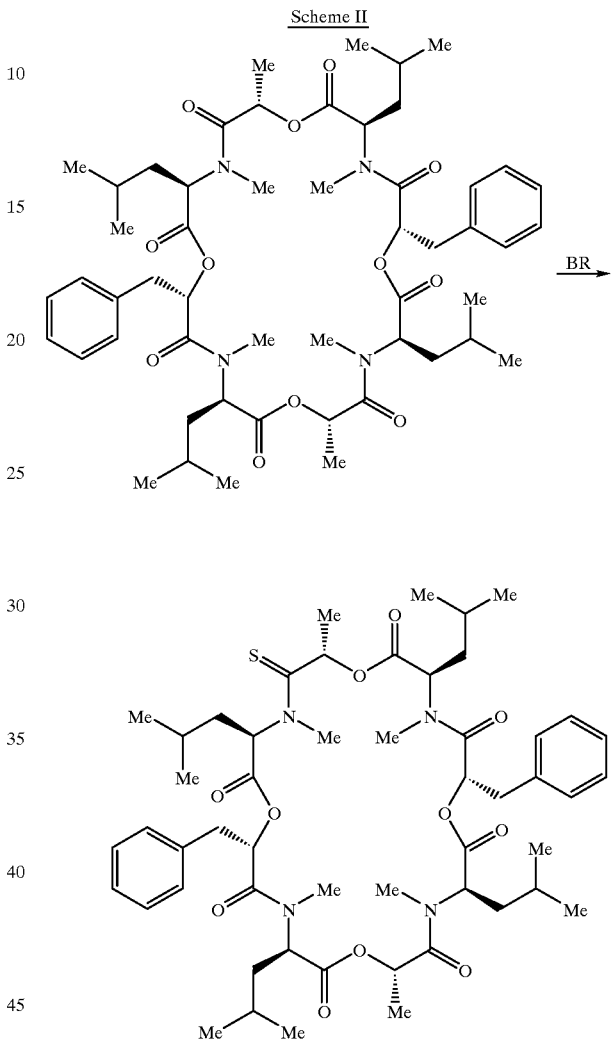

BR: Belleau's Reagent

The compounds required as starting materials in the practice of the process are defined in a general way by the formulae (II). In the formulae, those radicals which have already been mentioned in connection with the description of the substances of the formula (I) according to the invention as being preferred for these substituents preferably represent $R^1$ to $R^{12}$.

Some of the cyclic depsipeptides used as starting materials are known and can be prepared by methods known from the literature by fermentation or total synthesis [cf. Fermentation of the cyclooctadepsipeptides: PF 1022A: Fermentation from *Mycelia sterilia* (FERM BP-2671; prior name FERM P-10 504) in EP-A (European Published Specification) 382 173; T. Sasaki et al., J. Antibiotics 45, 1992, p. 692; U.S. Pat. No. 5,116,815; EP-A (European Published Specification) 503 538; Y. Kodama et al., Sci. Reports of Meiji Seika Kaisha 31, 1992, p. 1–8 from the same culture were isolated: PF 1022B, PF 1022C and PF 1022D; JP Pat. 5170 749; PF 1022E: JP Pat. 6 184 126;

unpublished PCT application PCT 965190; Total synthesis of the cyclooctadepsipeptides: JP-Pat. 5 229 997; JP Pat. 5 320 148; Makoto Ohyama et al., Biosci. Biotech. Biochem., 58 *(6), 1994, p. 1193; Makoi Kobayashi et al., Annu. Rep. Sankyo Res. Lab. 46, 1994, p. 67; Stephen J. Nelson et al., J. Antibiotics 47 (11), 1994, p. 1322; J. Scherkenbeck et al. Tetrahedron 51 (31), 1995, p. 8459 (PF 1022A); B. H. Lee Tetrahedron Lett. 38 (5), 1997, p. 757; WO 93/19 053; EP-A (European Published Specification) 634 408; WO 94/19 334; WO 95/07 272; EP-A (European Published Specification) 626 375; EP-A (European Published Specification) 626 376; EP-A (European Published Specification) 664 297; EP 718 293; WO 96/11945; WO 97/11 064 and also WO 97/09 331 and WO 97/02 2563].

A large number of different sulfurizing agents are described in the literature, such as, for example, hydrogen sulfide ($H_2S$), hydrogen sulfide/hydrogen chloride ($H_2S/HCl$), hydrogen persulfide/hydrogen chloride ($H_2S_2/HCl$), di-(ethylaluminium) sulfide [$(Et_2Al)_2S$], polymeric ethylaluminium sulfide [$(EtAlS)_n$], silicon disulfide ($SiS_2$), diboron trisulfide ($B_2S_3$), phosphorus pentachloride/dialuminium trisulfide/sodium sulfate ($PCl_5/Al_2S_3/Na_2SO_4$), sodium sulfide/sulfuric acid ($Na_2S/H_2SO_4$), diphosphorus pentasulfide ($P_2S_5$), diphosphorus pentasulfide/pyridine ($P_2S_5/Py$), diethylthiocarbamoyl chloride, diphosphorus pentasulfide/triethylamine ($P_2S_5/NEt_3$), diphosphorus pentasulfide/n-butyllithium ($P_2S_5$/n-BuLi), diphosphorus pentasulfide/sodium bicarbonate ($P_2S_5/NaHCO_3$; "Scheeren's Reagent", formation of $Na^{2+}[P_4S_{10}O]^{2-}$), diphosphorus pentasulfide/methanol ($P_2S_5$/MeOH), SCN-CO- OEt, $PSCl_x(NMe_2)_{3-x}$ (X=0–3), bis (tricyclohexyltin) sulfide/boron trihalide [$(C_6H_{11})_3Sn]S_2+ BX_3$ (X=Cl, F), EP 0 280 867 (1988), bis(1,5-cyclooctanediylboryl) sulfide [$(9-BBN)_2S$] as sulfurizing agent or as phosphorus pentasulfide substitute 2,4-bis-(methylthio)-1,3,2,4-dithiadiphosphetan-2,4-disulfide "Davy Reagent Methyl" (DR-Me), 2,4-bis-(ethylthio) 1,3, 2,4-dithiadiphosphetan-2,4-disulfide, "Davy Reagent Ethyl" (DR-Et), 2,4-bis-(p-tolylthio)-1,3,2,4-dithiadiphosphetan-2, 4-disulfide "Davy Reagent p-Tolyl or Heimgartner Reagent" (DR-T), 2,4-bis-(4-phenoxyphenyl)-2,4-dithioxo-1,3,2,4-dithiadiphosphetan "Belleau's Reagent (BR)", 2,4-bis-(4-phenylthiophenyl)-2,4-dithioxo-1,3,2,4-dithiadiphosphetan, 2,4-bis-(4-methoxyphenyl)-2,4-dithioxo-1,3,2,4-dithiadiphosphetan "Lawesson's Reagent (LR)" (cf. Davy Reagent: H. Heimgartner et al., Helv. Chim. Acta 70, 1987, p. 1001; Belleau's Reagent: Tetrahedron 40, 1984, p. 2047; Tetrahedron 40, 1984, p. 2663; Tetrahedron Letters 24, 1983, p. 3815; I. Thomson et al., Org. Synth. 62, 1984, p. 158 and literature cited therein; D. Brillon Synthetic Commun. 20 (19), 1990, p. 3085 and literature cited therein; selective thionation of oligopeptides: K. Clausen et al., J. Chem. Soc., Perkin Trans I 1984, 785; O. E. Jensen et al., Tetrahedron 41, 1985, p. 5595; Reviews on "Lawesson's Reagent, (LR)": R. A. Cherkasov et al., Tetrahedron 41, 1985, p. 2567; M. P. Cava et al., Tetrahedron 41, 1995, p. 5061; Diboryl sulfide: Liebigs Ann. Chem. 1992, p. 1081 and literature cited therein; Metzner et al. in Sulfur Reagents in Organic Synthesis, B. Harcourt: London 1994, Academic Press, p. 44–45).

Alternatively, reaction sequences are possible, such as, for example, an O-alkylation with $R_3O^+BF_4^-$ (R: -methyl, ethyl) (H. Meerwein et al., Justus Liebigs Ann. Chem. 641, (1961) p. 1) and subsequent reaction of the intermediates with anhydrous NaSH (R. E. Eibeck, Inorg. Syn. 7, (1963) p. 128), the in situ formation of chloroiminium salts and subsequent reaction with tetrathiomolybdates, in particular benzyltriethylammonium tetrathiomolybdate [$(Ph—CH_2—NEt_3)_2MoS_4$] (Tetrahedron Lett. 36 (45), 1995, p. 8311) or Hexamethyldisilathian ($TMS_2S$) (TMS: Trimethylsilyl; P. L. Fuchs et al., J. Org. Chem. 59, 1994, p. 348).

Preferred sulfurizing agents in the practice of the process 2 according to the invention are phosphorus reagents such as, for example, diphosphorus pentasulfide ($P_2S_5$), diphosphorus pentasulfidelpyridine ($P_2S_5/Py$), diphosphorus pentasulfidel triethylamine ($P_2S_5/NEt_3$), diphosphorus pentasulfide/sodium bicarbonate ($P_2S_5/NaHCO_3$ "Scheeren's Reagent") or, particularly preferably, the racemization-free 2,4-bis-(4-methoxyphenyl)-2,4-dithioxo-1,3,2,4-dithiadiphosphetan (LR: Lawesson's Reagent) (K. Clausen, M. Thorsen, S. -O. Lawesson Tetrahedron 37, 1981, p. 3635) 2,4-bis-(4-phenoxyphenyl)-2,4-dithioxo-1,3,2,4-dithiadiphosphetan "Belleau's Reagent (BR)" or 2,4-bis-(4-phenylthiophenyl)-2,4-dithioxo-1,3,2,4-dithiadiphosphetan.

Generally, it is advantageous to carry out the process according to the invention in the presence of diluents. The diluents are advantageously used in such an amount that the reaction mixture remains easily stirrable during the entire process. Suitable diluents for carrying out the process according to the invention are all inert organic solvents.

Examples include: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethylamine, triethylamine, tripropylamine, tributylamine, N-methyl-morpholine, pyridine and tetramethylenediamine, nitrohydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile, and compounds such as tetrahydrothiophene dioxide and dimethyl sulfoxide, tetramethylene sulfoxide, dipropyl sulfoxide, benzyl methyl sulfoxide, diisobutyl sulfoxide, dibutyl sulfoxide, diisoamyl sulfoxide; sulfones, such as dimethyl sulfone, diethyl sulfone, dipropyl sulfone, dibutyl sulfone, diphenyl sulfone, dihexyl sulfone, methyl ethyl sulfone, ethyl propyl sulfone, ethyl isobutyl sulfone and pentamethylene sulfone; aliphatic, cycloaliphatic or aromatic hydrocarbons, such as pentane, hexane, heptane, octane, nonane and industrial hydrocarbons, for example white spirits with components having boiling points in the range for example from 40° C. to 250° C., cymene, benzine fractions within a boiling point range from 70° C. to 190° C., cyclohexane, methylcyclohexane, petroleum ether, ligroin, octane, benzene, toluene, chlorobenzene, bromobenzene, xylene; esters, such as methyl acetate, ethyl acetate, butyl acetate, isobutyl acetate, and dimethyl carbonate, dibutyl carbonate, ethylene carbonate; amides, such as hexamethylenephosphoric triamide, formamide, N-methyl-forinamide, N,N-dimethylformamide, N,N-dipropylformamide, N,N-dibutylformamide, N-methyl-pyrrolidine, N-methyl-caprolactam, 1,3-dimethyl-3,4,5,6-tetrahydro-2(1H)- pyrimidine, octylpyrrolidone, octylcaprolactam, 1,3-dimethyl-2-imidazolidinone, N-formyl-piperidine, N,N'-1,4-diformylpiperazine; ketones, such as acetone, acetophenone, methyl ethyl ketone, methyl butyl ketone.

The process according to the invention can of course also be carried out in mixtures of the solvents and diluents mentioned.

The diluents to be used depend on the sulfurizing agent employed in each case.

However, preferred diluents for the thionation are aromatic hydrocarbons such as benzene, toluene, chlorobenzene, bromobenzene, nitrobenzene or xylene, ethers, such as ethyl propyl ether, methyl tert-butyl ether, anisole, phenetole, cyclohexyl methyl ether, tetrahydrofuran or dioxane.

The thionation according to process 2 is carried out by reacting the depsipeptides of the general formula (II) in the presence of a suitable sulfurizing agent, for example 2,4-bis-(4-methoxyphenyl)-2,4-dithioxo-1,3,2,4dithiadiphosphetan (LR: Lawesson's Reagent), 2,4-bis-(4-phenoxyphenyl)-2,4-diothioxo-1,3,2,4-dithiadiphosphetan (BR: Belleau's Reagent) or 2,4-bis-(4-phenylthiophenyl)-2,4-dithioxo-1,3,2,4-dithiadiphosphetan in one of the diluents mentioned.

The reaction time is from 10 minutes to 72 hours. The reaction is carried out at temperatures between −10° C. and +200° C., preferably between 0° C. and +150° C., particularly preferably at temperatures between +10° C. and +130° C. or at the boiling temperature of a suitable diluent. The reaction can generally be carried out under atmospheric pressure. The reaction is preferably carried out at atmospheric pressure or at pressures of up to 15 bar. and, if required, under an inert gas atmosphere (nitrogen or helium).

In the practice of the process 2 according to the invention, generally 0.5 to 3.5 mol, preferably 1.0 to 2.5 mol, of suifurizing agent are used per amide carbonyl group present in compounds of the general formula (II).

After the thionation has ended, the entire reaction mixture is cooled, separated off from precipitated thionizing agent and, if appropriate, washed. The products obtained can be purified in a conventional manner by recrystallization, vacuum distillation or column chromatography (see also the preparation examples).

Employing the process, thiodepsipeptides are obtainable, while retaining the original configuration of the starting materials, from the individual building blocks having (S) and (R) configuration (or L and D configuration).

The "inert solvents" in the aforementioned process variants are in each case solvents which are inert under the respective reaction conditions, but which do not have to be inert under all conceivable reaction conditions.

The active compounds are suitable for controlling pathogenic endoparasites encountered in humans and in animal husbandry and livestock breeding, in productive livestock, breeding stock, zoo animals, laboratory animals, animals used in experiments, and pets, and have low toxicity towards warm-blooded animals. They are active against resistant and normally sensitive species and against all or some stages of development of the pests. By controlling the pathogenic endoparasites, it is intended to reduce disease, mortality and decreasing performance (for example in the production of meat, milk, wool, hides, eggs, honey, etc.), so that more economical and simpler animal keeping is possible by using the active compounds. The pathogenic endoparasites include Cestodes, Trematodes, Nematodes and Acantocephales, in particular:

From the order of the Pseudophyllidea, for example Diphyllobothrium spp., Spirometra spp., Schistocephalus spp., Ligula spp., Bothridium spp., Diphlogonoporus spp.

From the order of the Cyclophyllidea, for example Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example Gyrodactylus spp., Dactylogyrus spp., Polystoma spp.

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomnum spp., Calicophoron spp, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.

From the order of the Enoplida, for example Trichuris spp., Capillaria spp., Trichomosoides spp., Trichinella spp.

From the order of the Rhabditida, for example Micronema spp., Strongyloides spp.

From the order of the Strongylida, for example Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example Oxyuris spp., Enterobius spp., Passalurus spp., Syphacia spp., Aspiculuris spp., Heterakis spp.

From the order of the Ascaridia, for example Ascaris spp., Toxascaris spp., Toxocara spp., Parascaris spp., Anisakis spp., Ascaridia spp.

From the order of the Spirurida, for example Gnathostoma spp., Physaloptera spp., Thelazia spp., Gongylonema spp., Habronema spp., Parabronema spp., Draschia spp., Dracunculus spp.

From the order of the Filariida, for example Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example Filicollis spp., Moniliformis spp., Macracanthorhynchus spp., Prosthenorchis spp.

The livestock and breeding stock include mammals, such as, for example, cattle, horses, sheep, pigs, goats, camels, water buffalo, donkeys, rabbits, fallow deer, reindeer, fur-bearing animals, such as, for example, minks, chinchilla or racoon, birds, such as, for example chickens, geese, turkeys or ducks, freshwater fish and sea fish, such as, for example, trout, carp and eels, reptiles and insects, such as, for example, honey bee and silkworm.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the habitat or with the aid of shaped articles containing the active compound, such as, for example, strips, plates, tapes, collars, ear tags, limb bands or marking devices.

Enteral administration of the active compounds is effected for example orally in the form of powders, tablets, capsules, pastes, drinks, granules, solutions, suspensions and emulsions which can be applied orally, boluses, medicated feed or drinking water. Dermal application is effected, for example, in the form of dipping, spraying, or pouring-on and spotting-on. Parenteral administration is effected, for example, in the form of injection (intramuscular, subcutaneous, intravenous or intraperitoneal) or by implants.

Suitable preparations include:

Solutions, such as solutions for injection, oral solutions, concentrates for oral administration after dilution, solutions for use on the skin or in body cavities, pour-on formulations, gels;

Emulsions and suspension for oral or dermal administration and for injection; semisolid preparations;

Formulations in which the active compound is incorporated in a cream base or in an oil-in-water or water-in-oil emulsion base;

Solid preparations, such as powders, premixes or concentrates, granules, pellets, tablets, boluses, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

Suitable solvents include: physiologically acceptable solvents, such as water, alcohols, such as ethanol, butanol, benzyl acohol, glycerol, propylene glycol, polyethylene glycols and N-methyl-pyrrolidone, and their mixtures.

If appropriate, the active compounds can also be dissolved in physiologically acceptable vegetable or synthetic oils which are suitable for injection.

Suitable solubilizers include: solvents which facilitate the dissolution of the active compound in the main solvent or which prevent precipitation of the active cornpound. Examples of solubilizers are polyvinylpyrrolidone, polyethoxylated castor oil and polyethoxylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on. These solutions are prepared as described above in the case of the solutions for injection.

It may be advantageous to add thickeners in the preparation process. The following are thickeners: inorganic thickeners, such as bentonites, colloidal silica, aluminum monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described for the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other auxiliaries, such as colorants, absorption promoters, antioxidants, photostabilizers or tackifiers are added.

Suitable solvents include: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methylpyrrolidone, or 2,2-dimethyl-4-oxymethylene-1,3-dioxolane.

Colorants are all colorants which can be dissolved or suspended and which are approved for use in animals.

Examples of absorption promoters are DMSO, spreading oils, such as isopropyl myristate, dipropylene glycol pelargonate, silicone oils, fatty acid esters, triglycerides or fatty alcohols.

The following are antioxidants: sulfites or metabisulfites, such as potassium metabisulfite, ascorbic acid, butylhydroxytoluene, butylhydroxyanisole or tocopherol.

Example of photostabilizers are novantisolic acid.

Tackifiers are, for example, cellulose derivatives, starch derivatives, polyacrylates or natural polymers such as alginates or gelatin.

Emulsions can be administered orally, dernally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, absorption promoters, preservatives, antioxidants, photostabilizers, and viscosity-increasing substances.

Suitable hydrophobic phases (oils) include: paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid having a medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

Suitable hydrophilic phases include: water, alcohols, such as, for example, propylene glycol, glycerol, sorbitol and their mixtures.

Suitable emulsifiers include: nonionic surfactants, for example polyethoxylated castor oil, polyethoxylated sorbitan monooleate, sorbitan monostearate, glycerol monostearate, polyoxyethyl stearate or alkylphenol polyglycol ethers;

Ampholytic surfactants, such as disodium N-lauryl—iminodipropionate or lecithin;

Anionic surfactants, such as Na lauryl sulfate, fatty alcohol ether sulfates, and the monoethanolamine salt of monoldialkylpolyglycol ether orthophosphoric ester;

Suitable other auxiliaries include: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, absorption promoters, preservatives, antioxidants and photostabilizers.

Suitable liquid excipients include all homogeneous solvents and solvent mixtures.

Suitable wetting agents (dispersants) include the surfactants indicated fuirther above.

Suitable other auxiliaries include those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, common salt, carbonates, such as calcium carbonate, hydrogen carbonates, aluminum oxides, silicas, clays, precipitated or colloidal silica, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and glidants, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active compounds can also be present in mixtures with synergists or other active compounds which are active against pathogenic endoparasites.

Examples of such active compounds are L-2,3,5,6tetrahydro-6-phenyl-imidazothiazole, benzimidazole carbamates, praziquantel, pyrantel or febantel.

Ready-to-use preparations contain the active compound in concentrations of 10 ppm to 20 percent by weight, preferably from 0.1 to 10 percent by weight. Preparations which are diluted before use contain the active compound in concentrations of 0.5 to 90 percent by weight, preferably from 5 to 50 percent by weight.

EXAMPLE A

In vivo Nematode Test

*Heterakis spumosa*/Mouse

Mice are experimentally infected with nematodes of the variety *Heterakis spumosa*. In order to infect the mice, 90 embryonate *Heterakis spumosa* eggs are applied orally.

After the prepotency time had elapsed, the suspended active compounds are applied orally and/or intraperitoneally on the 46th day after the infection.

Determination of Effectiveness:

The mice are selected on the 54th day after the infection. The adult parasites in the colon and caecum are counted with the aid of a microscope. The treatment results in the doses group are compared with the untreated control group.

Active compounds tested and effective dosage rates (dosis effectiva) can be seen from the table which follows.

| Active compound Example No. | Effective dosage rates in [mg/kg] | Reduction rate in [%] |
|---|---|---|
| PF 1022A | 50 | 0 |
| 1 | 50 | 100 |

EXAMPLE B

In vivo Nematode Test

*Haemonchus contortus*/Sheep

Sheep which had been experimentally infected with *Haemonchus contortus* were treated after the prepotency time of the parasite had elapsed. The active compounds were applied orally and/or intravenously as pure active compound.

The degree of effectiveness is determined by quantitatively counting the worm eggs which have been excreted with the faeces before and after the treatment.

A complete cessation of egg excretion after the treatment means that the worms have been aborted or damaged to such an extent that they no longer produce eggs (dosis effectiva).

Active compounds tested and effective dosage rates can be seen from the table which follows

| Active compound Example No. | Effective dosage rates in [mg/kg] |
|---|---|
| Cyclo(-MeLeu-D-Lac-MeLeu-D-PhLac-)$_2$ (PF 1022A) | 0.25 |
| Cyclo(-MeLeu-D-Lac-MeLeu-D-4-MorPhLac-)$_2$ | 0.05 |
| 1 | 0.10 |
| 3 | 0.025 |
| 6 | 0.01 |
| 7 | 0.01 |
| 8 | 0.01 |
| 10 | 0.01 |
| 12 | 0.01 |

D-4-MorPhLac: D-4-Morpholinophenyllactate

PREPARATION EXAMPLES

Example 1

Cyclo(-N-methyl-L-leucyl-D-thiolactyl-N-methyl-L-leucyl-D-phenylthiolactyl-N-methyl-L-leucyl-D-thiolactyl-N-methyl-L-leucyl-D-phenylthiolactyl-)

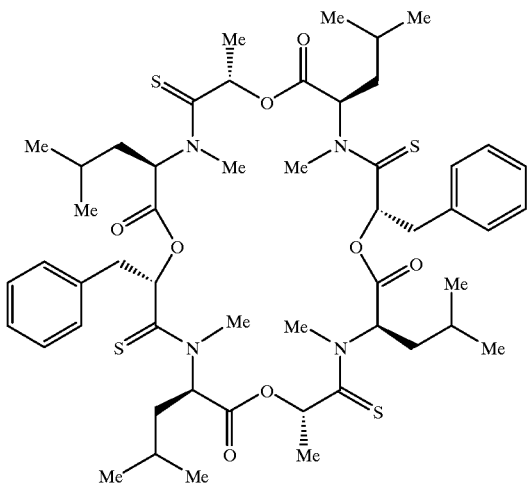

1.0 g (1.05 mmol) of cyclo(-N-methyl-L-leucyl-D-lactyl-N-methyl-L-leucyl-D-phenyllactyl-N-methyl-L-leucyl-D-lactyl-N-methyl-L-leucyl-D-phenyllactyl-) PF 1022A (cf EP-A (European Published Specification) 382 173, U.S. Pat. No. 5,116,815) in 20 ml of toluene was admixed with 1.4 g (3.5 mmol) of 2,4-bis-(4-methoxy-phenyl)-2,4-dithioxo-1,3,2,4dithiadiphosphetan ("Lawessor's Reagent") and stirred at reflux temperature for 3.5 hours. The entire reaction mixture is then cooled to 0° C. and filtered, and the filtrate obtained is concentrated under reduced pressure. The crude product obtained is chromatographed over a silica gel column (silica gel 60—Merck, particle size: 0.04 to 0.063 mm), eluting first with methylene chloride and then with cyclohexane:acetone (3:1). 0.46 g (43.6% of theory) of cyclo(-N-methyl-L-leucyl-D-thiolactyl-N-methyl-L-leucyl-D-phenylthiolactyl-N-methyl-L-leucyl-D-thiolactyl-N-methyl-L-leucyl-D-phenylthiolactyl-) are obtained.

$^1$H NMR (CDCl$_3$, δ): 2.99, 3.06, 3.26, 3.42 (4×—N—Me); 4.86, 6.42, 6.61 (4×—N—CH$_2$—); 5.31, 5.55, 5.81, 5.89 (4×—O—CH$_2$—); 7.26 (phenyl-H) ppm.

LC-MS (acidic) m/z (%): 1013 (M$^+$, 100); 310 (21); 274 (30); 198 (42). C$_{52}$H$_{76}$N$_4$O$_8$S$_4$ (1013.4)

Example 2

Cyclo(-N-melhyl-L-leucyl-D-thiolactyl-N-methyl-L-leucyl- D-4-nitro-phenylthiolactyl-N-methyl-L-leucy-D-thiolactyl-N-methyl-L-leucyl-D-4-nitro-phenylthiolactyl-)

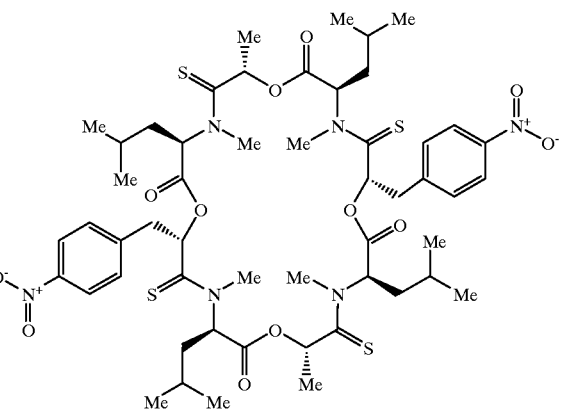

The thionation is carried out similarly to the reaction procedure of Example 1, using:
0.50 g (0.48 mmol) of cyclo(-N-methyl-L-leucyl-D-lactyl-N-methyl-L-leucyl-D-4-nitro-phenyllactyl-N-methyl-L-leucyl-D-lactyl-N-methyl-L-leucyl-D-4-nitro-phenyllactyl-) (cf WO 93/19 053, EP-A (European Published Specification) 634 408)
0.65 g (1.59 mmol) of 2,4-bis-(4-methoxyphenyl)-2,4-dithioxo-1,3,2,4-dithiadiphosphetan ("Lawesson's Reagent")
10 ml of absolute toluene The crude product obtained is chromatographed over a silica gel column (silica gel 60—Merck, particle size: 0.04 to 0.063 mm), eluting first with methylene chloride and then with cyclohexane:acetone (3:1). 0.34 g (63.8% of theory) of cyclo(-N-methyl-L-leucyl-D-thiolactyl-N-methyl-L-leucyl-D-4-nitrophenylthiolactyl-N-methyl-L-leucyl-D-thiolactyl-N-methyl-L-leucyl-D-4-nitrophenylthiolactyl-) is obtained.

$^1$H NMR (CDCl$_3$, δ): 3.04, 3.09, 3.25, 3.50 (4×—N—Me); 4.87, 6.38, 6.56, 6.63 (433 —N—CH$_2$—); 5.31, 5.52, 5.81, 5.91 (4×—O—CH$_2$—); 8.17, 7.46 (aryl-H) ppm.

LC-MS (acidic) m/z (%): 1103 (M+H, 100); 392 (38); 177 (40); 136 (30). C$_{52}$H$_{74}$N$_6$O$_{12}$S$_4$ (1103.4)

Example 3

Cyclo(-N-methyl-L-leucyl-D-thiolactyl-N-melhyl-L-leucyl-D-4-N-morpholinophenylthiiolactyl-N-methyl-L-leucyl-D-thiolactyl-N-methyl-L-leucyl-D-4-N-morpholinophenylthiolactyl-)

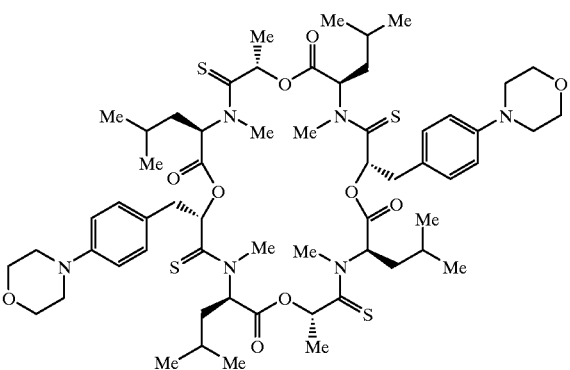

The thionation is carried out similarly to the reaction procedure of Example 1, using:

- 0.50 g (0.44 mmol) of cyclo (-N-methyl-L-leucyl-D-lactyl-N-methyl-L-leucyl-D4-N-morpholinophenyl-lactyl-N-methyl-L-leucyl-D-lactyl-N-methyl-L-leucyl-D-4-N-morpholinophenyllactyl-) (cf WO 93/19 053, EP-A (European Published Specification) 634 408)
- 0.60 g (1.48 mmol) of 2,4-bis-(4-methoxy-phenyl)-2,4-dithioxo-1,3,2,4-dithiadiphosphetan ("Lawesson's Reagent")
- 10 ml of absolute toluene The crude product obtained is chromatographed over a silica gel column (silica gel 60—Merck, particle size: 0.04 to 0.063 mm), eluting first with methylene chloride and then with cyclohexane:acetone (3:1). 0.37 g (70.0% of theory) of cyclo(-N-methyl-L-leucyl-D-thio-lactyl-N-methyl-L-leucyl-D4-N-morpholino-phenylthiolactyl-N-methyl-L-leucyl-D-thiolactyl-N-methyl-L-leucyl-D-4-N-morpholinophenylthiolactyl-) is obtained.

$^1$H NMR (CDCl$_3$, δ): 3.01, 3.08, 3.26, 3.40 (4×—N—Me); 3.12, 3.85 (2×Mor); 4.85, 6.42, 6.62 (4×—N—CH$_2$—); 5.30, 5.55, 5.78, 5.88 (4×—O—CH$_2$—); 6.81, 7.26 (aryl-H) ppm.

LC-MS (acidic) m/z (%): 1184 (M+H, 100); 986 (13); 593 (32); 392 (73); 177 (78). C$_{60}$H$_{90}$N$_6$O$_{10}$S$_4$ (1183.6)

Example 4

Cyclo(-N-methyl-L-leucyl-D-thiolactyl-N-methyl-L-leucyl-D-4-(fur-2-yl-methoxy)-phenylthiolactyl-N-methyl-L-leucyl-D-thiolacoyl-N-methyl-L-leucyl-D-phenylthiolactyl-)

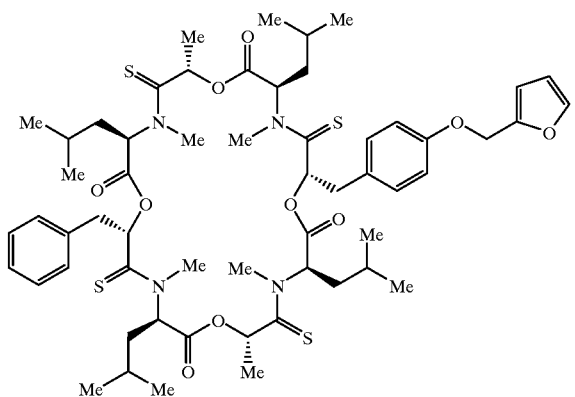

The thionation is carried out similarly to the reaction procedure of Example 1, using:

- 0.50 g (0.48 mmol) of cyclo(-N-methyl-L-leucyl-D-lactyl-N-methyl-L-leucyl-D-4-(fur-2-yl-methoxy)-phenyllactyl-N-methyl-L-leucyl-D-lactyl-N-methyl-L-leucyl-D-phenyllactyl-) (cf. WO 97/11 064)
- 0.64 g (1.58 mmol) of 2,4-bis-(4-methoxy-phenyl)-2,4-dithioxo-1,3,2,4-dithiadiphosphetan ("Lawesson's Reagent") 10 ml of absolute toluene The crude product obtained is chromatographed over a silica gel column (silica gel 60—Merk, particle size: 0.04 to 0.063 mm), eluting first with methylene chloride and then with cyclohexane:acetone (3:1). 0.14 g (26.6% of theory of cyclo (-N-mehtyl-L-leucyl-D-thiolactyl-N-methyl-L-leucyl-D-4-(fur-2-yl-methoxy)-phenylthiolactyl-N-methyl-L-leucyl-D-thiolactyl-N-methyl-L-leucyl-D-phenylthiolactyl-) is obtained.

mp.: 120–125° C.

$^1$H NMR (CDCl$_3$, δ): 3.15, 3.21, 3.42, 3.57 (4×—N—Me); 5.03, 6.55, 6.78 (4×—N—CH$_2$—); 5.45, 5.69, 5.89–6.08 (4×—O—CH$_2$—); 7.05–7.60 (aryl-H, furyt-H) ppm.

LC-MS (loop) m/z (%): 1109 (M$^+$, 2); 1108 (3); 370 (15); 274 (32). C$_{57}$H$_{80}$N$_4$O$_{10}$S$_4$ (1109.54)

Example 5

Cyclo(-N-methyl-L-leucyl-D-thiolactyl-N-methyl-L-leucyl-D-4-(fur-2-yl-methoxy)-phenylthiolactyl-N-methyl-L-leucyl-D-thiolactyl-N-methyl-L-leucyl-D-4-(fur-2-yl-methoxy)-phenylthiolactyl-)

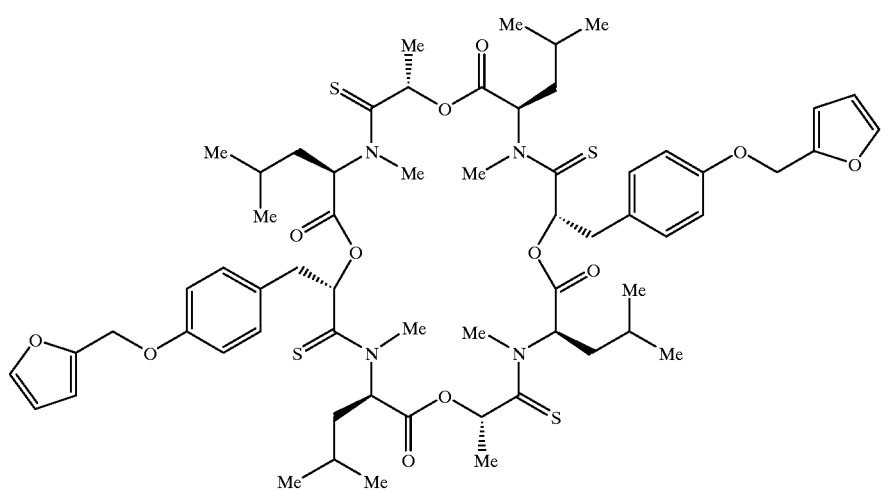

The thionation is carried out similarly to the reaction procedure of Example 1, using:

0.50 g (0.44 mmol) of cyclo(-N-methyl-L-leucyl-D-lactyl-N-methyl-L-leucyl-D-4-(fur-2-yl-methoxy)-phenyllactyl-N-methyl-L-leucyl-D-lactyl-N-methyl-L-leucyl-D-4-(fur-2-yl-methoxy)-phenyllactyl-) (cf. WO 97/11 064)

0.58 g (1.44 mmol) of 2,4-bis-(4-methoxyphenyl)-2,4-dithioxo-1,3,2,4-dithiadiphosphetan ("Lawesson's Reagent")

10 ml of absolute toluene

The crude product obtained is chromatographed over a silica gel column (silica gel 60—Merck, particle size: 0.04 to 0.063 mm), eluting first with methylene chloride and then with cyclohexane:acetone (3:1). 0.12 g (22.7% of theory) of cyclo (-N-methyl-L-leucyl-D-thiolactyl-N-methyl-L-leucyl-D4-(fur-2-yl-methoxy)-phenylthiolactyl-N-methyl-L-leucyl-D-thiolactyl-N-methyl-L-leucyl-D-4-(fur-2-yl-methoxy)-phenylthiolactyl-) is obtained.

mp.: 107–110° C.

$^1$H NMR (CDCl$_3$, δ): 3.01, 3.07, 3.26, 3.41 (4×—N—Me); 4.96 (2×—O—CH$_2$—); 4.86, 6.42, 6.62 (4×—N—CH$_2$—); 5.32, 5.56, 5.78, 5.85 (4×—O—CH$_2$—); 6.91–7.44 (aryl-H, furyl-H) ppm.

LC-MS (acid) m/z (%): 1205 (M$^{3O}$, 3); 1204 (5); 370 (41); 198 (100). C$_{62}$H$_{84}$N$_4$O$_{12}$S$_4$ (1205.6)

Example 6

Cyclo(-N-methyl-L-leucyl-D-thiolactyl-N-methyl-L-leucy-D-4-(pyrid-2-yl-methoxy)-phenylthiolactyl-N-methyl-L-leucy-D-thiolactyl-N-methyl-L-leucyl-D-4-(pyrid-2-yl-methoxy)-phenylthiolactyl-)

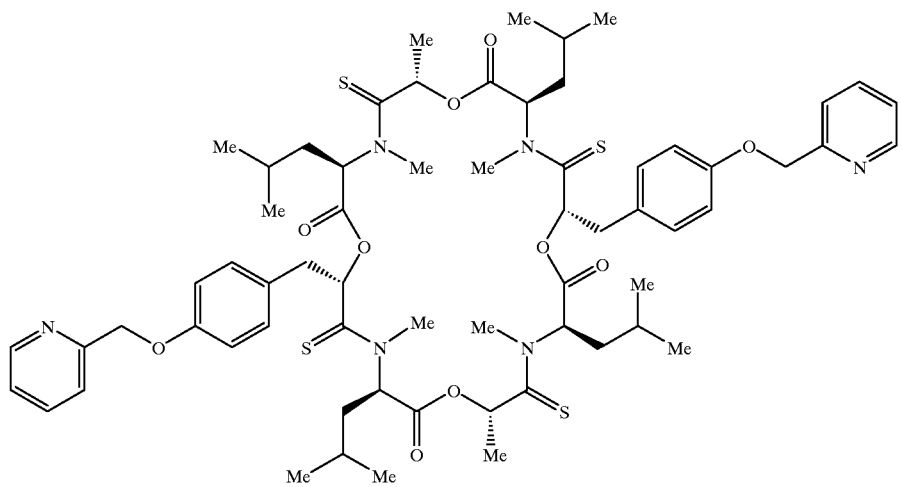

The thionation is carried out similarly to the reaction procedure of Example 1, using:

0.50 g (0.43 mmol) of cyclo(-N-methyl-L-leucyl-D-lactyl-N-methyl-L-leucyl-D-4-(pyrid-2-yl-methoxy)-phenyllactyl-N-methyl-L-leucyl-D-lactyl-N-methyl-L-leucyl-D-4-(pyrid-2-yl-methoxy)-phenyllactyl-) (cf WO 97/11 064)

0.57 g (1.41mmol) of 2,4-bis-(4-methoxyphenyl)-2,4-dithioxo-1,3,2,4-dithiadiphosphetan ("Lawesson's Reagent")

10 ml of absolute toluene

The crude product obtained is chromatographed over a silica gel column (silica gel 60—Merck, particle size: 0.04 to 0.063 mm), eluting first with methylene chloride and then with cyclohexane:acetone (3:1). 0.16 g (30.9% of theory) of cyclo (-N-methyl-L-leucyl-D-thiolactyl-N-methyl-L-leucyl-D4-(pyrid-2-yl-methoxy)-phenylthiolactyl-N-methyl-L-leucyl-D-thiolactyl-N-methyl-L-leucyl-D-4-(pyrid-2-yl-methoxy)-phenylthiolactyl-) is obtained.

$^{13}$C NMR (CDCl$_3$, δ): 34.8, 35.2, 37.1, 39.2 (N-Me); 71.8, 73.3, 75.4 (—CH—O—); 40.1, 40.6 (—CH$_2$—); 62.3, 62.5, 62.6 (—$\underline{C}$H—N—); 121.4, 122.8, 136.9, 149.4 (=$\underline{C}$H—, Py); 70.7 (—$\underline{C}$H$_2$—O—); 115.0, 130.9 (=$\underline{C}$H—, phenyl); 203.2, 203.4, 204.8, 205.7 (N—C=S); 168.8, 169.5, 170.0 (—O—C=O) ppm.

$^1$H-NMR (CDCl$_3$, ): 3.01, 3.19, 3.26, 3.41 (4×—N-Me); 5.17 (2×—O—CH$_2$); 4.86, 6.41, 6.64, 6.66 (4×—N—CH$_2$—); 5.31, 5.75, 5.57, 5.85 (4×—O—CH$_2$—); 6.91, 7.16 (phenyl-H), 7.24, 7.51, 7.72, 8.59 (pyridyl-H) ppm.

LC-MS (loop) m/z (%): 1228 (M⁺H, 18); 383 (58); 224 (100). $C_{64}H_{86}N_6O_{14}S_4$ (1227.68)

Example 7

Cyclo(N-methyl-L-leucyl-D-thiolactyl-N-methyl-L-leucyl-D-phenyllactyl-N-methyl-L-leucyl-D-lactyl-N-methyl-L-leucyl-D-phenyllactyl-)

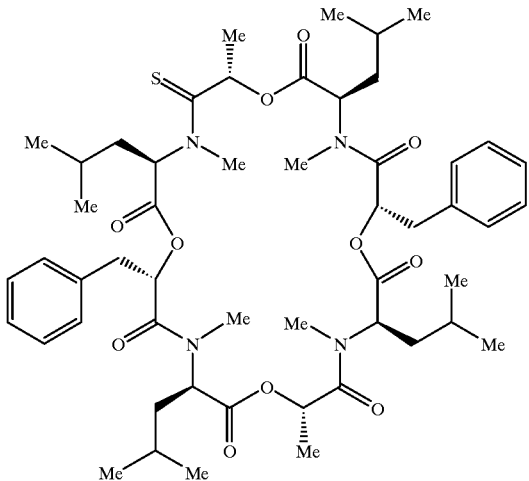

1.0 g (1.05 mmol) of cyclo-(N-methyl-L-leucyl-D-lactyl-N-methyl-L-leucyl-D-phenyllactyl-N-methyl-L-leucyl-D-lactyl-N-methyl-L-leucyl-D-phenyllactyl-) PF 1022A (cf EP-A (European Published Specification) 382173, U.S. Pat. No. 5,116,815) in 15 ml of tetrahydrofuran was mixed at 0° C. with 0.26 g (0.5 mmol) of 2,4-bis-( 4-phenoxyphenyl)-2,4-dithioxo-1,3,2,4-dithiadiphosphetan ("Belleau's Reagent") and stirred at room temperature for 18 hours. The entire reaction is then concentrated under reduced pressure. The crude product obtained is chromatographed twice over a silica gel column (silica gel 60—Merck, particle size: 0.04 to 0.063 mm), eluting with cyclohexane:acetone (3:1). 0.12 g (11.8% of theory) of cyclo(-N-methyl-L-leucyl-D-thiolactyl-N-methyl-L-leucyl-D-phenyllactyl-N-methyl-L-leucyl-D-lactyl-N-methyl-L-leucyl-D-phenyllactyl-) is obtained.

LC-MS (acidic) m/z (%): 965 (M³⁰, 100); 200 (45). $C_{52}H_{76}N_4O_{11}S$ (965.2)

Example 8

Cyclo(N-methyl-L-leucyl-D-thiolactyl-N-methyl-L-leucyl-D-4-N-morpholinophenyllactyl-N-methyl-L-leucyl-D-lactyl-N-methyl-L-leucyl-D-4-N-morpholinophenyllactyl-)

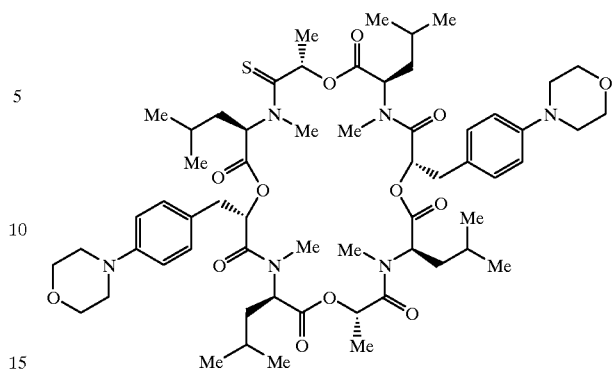

The thionation is carried out similarly to the reaction procedure of Example 7, using:

0.41 g (0.37 mmol) of cyclo(-N-methyl-L-leucyl-D-lactyl-N-methyl-L-leucyl-D-4-N-morpholinophenyllactyl-N-methyl-L-leucyl-D-lactyl-N-methyl-L-leucyl-D-4-N-morpholinophenyllactyl-) (cf WO 93/19 053, EP-A 634 408)

0.36 g (0.73 mmol) of 2,4-bis-(4-phenoxyphenyl)-2,4-dithioxo-1,3,2,4-dithiadiphosphetan ("Belleai's Reagent")

10 ml of absolute toluene

The crude product obtained is chromatographed over a silica gel column (silica gel 60—Merck, particle size: 0.04 to 0.063 mm), eluting with cyclohexane:acetone (3:1). 0.70 g (16.8% of theory) of cyclo(-N-methyl-L-leucyl-D-thiolactyl-N-methyl-L-leucyl-D-4-N-morpholinophenyllactyl-N-methyl-L-leucyl-D-lactyl-N-methyl-L-leucyl-D4-N-morpholinophenyllactyl-) is obtained.

LC-MS (acidic) m/z (%): 1135 (M³⁰, 56); 361 (100). $C_{60}H_{90}N_6O_{13}S$ (1135.4) $R_t$(HPLC): 16.53 min.

Example 9

Cyclo(N-methyl-L-leucyl-D-thiolactyl-N-methyl-L-leucyl-D-4-nitrophenyllactyl-N-methyl-L-leucyl-D-lactyl-N-methyl-L-leucyl-D-4-nitrophenyllactyl-)

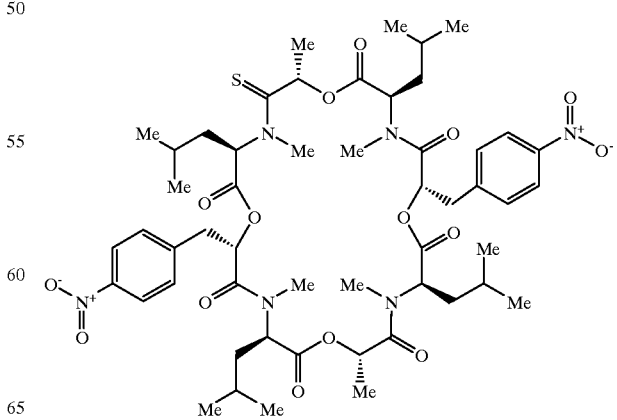

The thionation is carried out similarly to the reaction procedure of Example 7, using:

0.50 g (0.48 mmol) of cyclo(-N-methyl-L-leucyl-D-lactyl-N-methyl-L-leucyl-D-4-nitrophenyllactyl-N-methyl-L-leucyl-D-lactyl-N-methyl-L-leucyl-D4-nitrophenyllactyl-) (cf WO 93/19 053, EP-A 634 408)

0.24 g (0.48 mmol) of 2,4-bis-(4-phenoxyphenyl)-2,4-dithioxo-1,3,2,4-dithia-diphosphetan ("Belleau's Reagent")

10 ml of absolute tetrahydrofuran

The reaction mixture is stirred at 50° C. for 24 hours and concentrated under reduced pressure. The crude product obtained is chromatographed over a silica gel colummn (silica gel 60—Merck, particle size: 0.04 to 0.063 mm), eluting with cyclohexane:acetone (4:1). The product is subsequently purified once more using preparative HPLC (gradient: water/acetonitrile). 16 mg (3.1% of theory) of cyclo(-N-methyl-L-leucyl-D-thiolactyl-N-methyl-Leucyl-D-4-nitrophenyllactyl-N-methyl-L-leucyl-D-lactyl-N-methyl-L-leucyl-D-4-nitrophenyllactyl-) are obtained.

LC-MS (acidic) m/z (%): 1056 (M+H, 38). $C_{52}H_{74}N_6O_{15}S$ (1055.3)

$R_t$ (HPLC): 17.38 min.

Example 10

Cyclo(-N-methyl-L-leucyl-D-thiolactyl-N-methyl-L-leucyl-D-4-(pyrid-2-yl-methoxy)-phenyllactyl-N-methyl-L-keucyl-D-lactyl-N-methyl-L-leucyl-D-4-(pyrid-2-yl-methoxy)-phenyllactyl-)

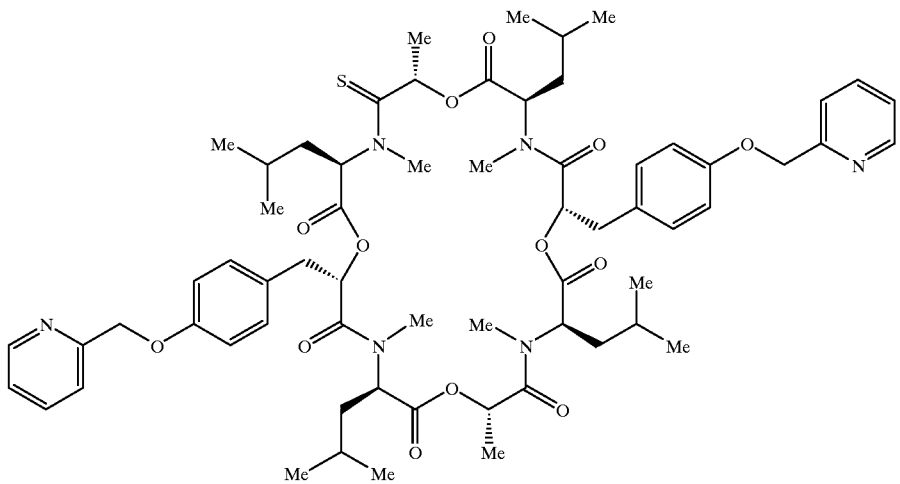

The thionation is carried out similarly to the reaction procedure of Example 9, using:

0.41 g (0.35 mmol) of cyclo(-N-methyl-L-leucyl-D-lactyl-N-methyl-L-leucyl-D-4-(pyrid-2-yl-methoxy)-phenyllactyl-N-methyl-L-leucyl-D-lactyl-N-methyl-L-leucyl-D-4-(pyrid-2-yl-methoxy)-phenyllactyl-) (cf WO 97/11 064)

0.52 g (1.05 mmol) of 2,4-bis-(4-phenoxyphenyl)-2,4-dithioxo-1,3,2,4-dithia-diphosphetan ("Belleau's Reagent")

10 ml of absolute tetrahydrofuran

The crude product obtained is chromatographed over a silica gel column (silica gel 60—Merck, particle size: 0.04 to 0.063 mm), eluting initially with methylene chloride and then with cyclohexane:acetone (4:1). 53.9 mg (13.0% of theory) of cyclo(-N-methyl-L-leucyl-D-thiolactyl-N-methyl-L-leucyl-D-4-(pyrid-2-yl-methoxy)-phenyllactyl-N-methyl-L-leucyl-D-lactyl-N-methyl-L-leucyl-D-4-(pyrid-2-yl)-methoxy)-phenyllactyl-) are obtained.

$^{13}$C-NMR (CDCl$_3$, δ): 204.9; 205.8 ppm (—NMe—$\underline{C}$=S)/2 conformational isomers.

LC-MS (loop) m/z (%): 1179 (M$^+$, 100). $C_{64}H_{86}N_6O_{13}S$ (1179.5)

Example 11

Cyclo(-N-methyl-L-leucyl-D-thiolactyl-N-methyl-L-leucyl-D-4-(fur-2-yl-methoxy)-phenyllactyl-N-methyl-L-leucyl-D-lactyl-N-methyl-L-leucyl-D-4-(fur-2-yl-methoxy)-phenyllactyl-)

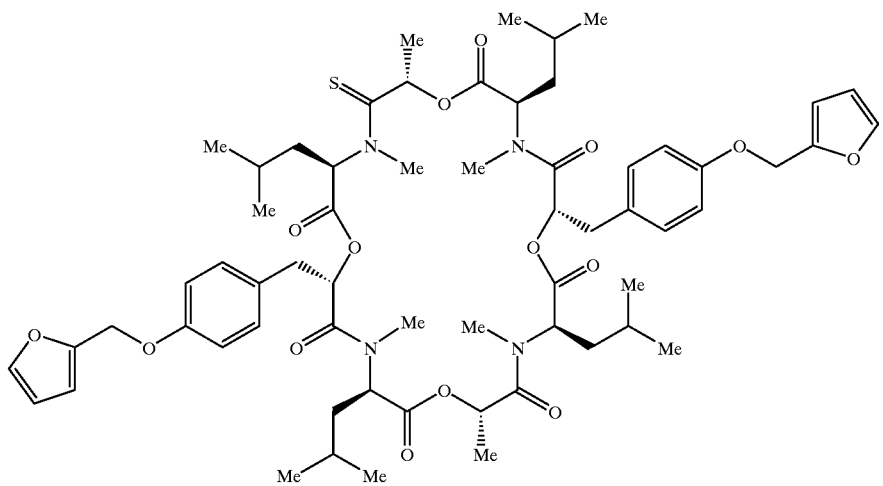

The thionation is carried out similarly to the reaction procedure of Example 9, using:

0.47 g (0.41 mmol) of cyclo(-N-methyl-L-leucyl-D-lactyl-N-methyl-L-leucyl-D-4-(fur-2-yl-methoxy)-phenyllactyl-N-methyl-L-leucyl-D-lactyl-N-methyl-L-leucyl-D-4-(fur-2-yl-methoxy)-phenyllactyl-) (cf WO 97/11 064)

0.20 g (0.41 mmol) of 2,4-bis-(4-phenoxyphenyl)-2,4-dithioxo-1,3,2,4-dithia-diphosphetan ("Belleauds Reagent")

10 ml of absolute tetrahydrofuran

The crude product obtained is chromatographed over a silica gel column (silica gel 60—Merck, particle size: 0.04 to 0.063 mm), eluting initially with methylene chloride and then with cyclohexane:acetone (4:1). 130 mg (27.3% of theory) of cyclo(-N-methyl-L-leucyl-D-thiolactyl-N-methyl-L-leucyl-D-4-(fur-2-yl-methoxy)-phenyllactyl-N-methyl-L-leucyl-D-lactyl-N-methyl-L-leucyl-D-4-(fur-2-yl-methoxy)-phenyllactyl-) are obtained.

$^{13}$C-NMR (CDCl$_3$, δ): 204.9; 205.8 ppm (—NMe—$\underline{C}$=S)/2 conformational isomers.

LC-MS (acidic) m/z (%): 1158 (M$^+$H, 100). C$_{62}$H$_{84}$N$_4$O$_{15}$S (1157.4)

R$_t$ (HPLC): 17.85 min.

Example 12

Cyclo(N-methyl-L-leucyl-D-thiolactyl-N-methyl-L-leucyl-D4-fur-2-yl-methoxy)-phenyllactyl-N-methyl-L-leucyl-D-lactyl-N-methyl-L-leucyl-D-phenyllactyl-)

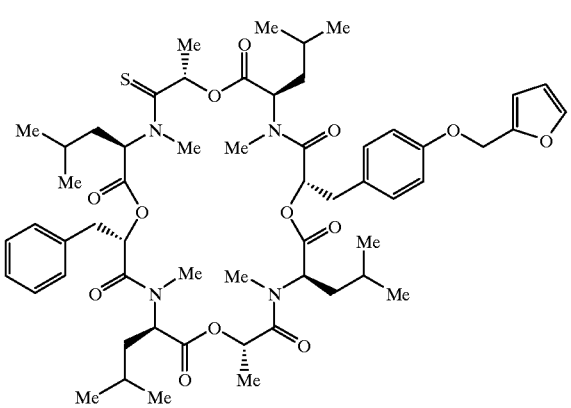

The thionation is carried out similarly to the reaction procedure of Example 9, using:

0.40 g (0.38 mmol) of cyclo(-N-methyl-L-lactyl-N-methyl-L-leucyl-D-4-(fur-2-yl-methoxy)-phenyllactyl-N-methyl-L-leucyl-D-lactyl-N-methyl-L-leucyl-D-phenyllactyl-) (cf WO 97/11 064)

0.20 g (0.38 mmol) of 2,4-bis-(4-phenoxyphenyl)-2,4-dithioxo-1,3,2,4-dithia-diphosphetan ("Belleau's Reagent")

10 ml of absolute tetrahydrofuran

The crude product obtained is chromatographed over a silica gel column (silica gel 60—Merck, particle size: 0.04 to 0.063 mm), eluting initially with methylene chloride and then with cyclohexane:acetone (4:1). 46.1 mg (11.4% of theory) of cyclo(-N-methyl-L-leucyl-D-thiolactyl-N-methyl-L-leucyl-D4-(fur-2-yl-methoxy)-phenyllactyl-N-metbyl-L-leucyl-D-lactyl-N-metbyl-L-leucyl-D-phenyllactyl-) are obtained.

LC-MS (loop) m/z (%): 1061 ($M^{30}$, 100). $C_{57}H_{80}N_4O_{13}S$ (1061.3) $R_t$(HPLC): 17.55 min.

What is claimed is:

1. Cyclic thiodepsipeptides of the formula (I) and salts thereof

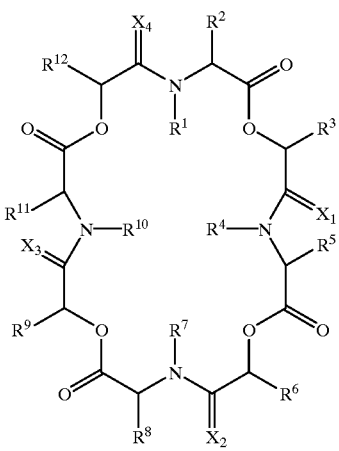

in which

R$^1$, R$^4$, R$^7$ and R$^{10}$ each represent independently of one another hydrogen, straight-chain or branched $C_{1-4}$-alkyl, and R$^2$, R$^5$, R$^8$ and R$^{11}$ each represent independently of one another hydrogen, straight-chain or branched $C_{1-8}$-alkyl, $C_{1-8}$-alkenyl, $C_{3-6}$-cycloalkyl, $C_{3-6}$-cycloalkyl-$C_{1-2}$alkyl, aryl-$C_{1-2}$-alkyl, hetaryl-$C_{1-2}$-alkyl, aryl or hetaryl, selected from the group consisting of benzyl, furyl and pyridinyl groups, each of which is optionally substituted, and R$^9$ and R$^{10}$ together with the atoms that they are attached to represent a 5- or 6-membered ring which may optionally be substituted, and R$^{10}$ and R$^{11}$ together with the atoms that they are attached to represent a 5-, 6- or 7-membered ring which may optionally be interrupted by oxygen, sulfur, sulfoxy or sulfonyl which ring is a member of cyclic amino groups having saturated and unsaturated monocyclic groups with a nitrogen atom as heteroatom selected from the group consisting of 1-azetidinyl, pyrrolidino, 2-pyrrolin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl or homopiperidinyl; a member of cyclic amino groups having saturated and unsaturated monocyclic groups with two or more nitrogen atoms as heteroatoms selected from the group consisting of 1-imidazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropyrimidin-1-yl, perhydropyrimidin-1-yl and 1,4-diazacyclo-heptan-1-yl; a member of cyclic amino groups having saturated and unsaturated monocyclic groups with one or two oxygen atoms and one to 3 nitrogen atoms as heteroatoms selected from the group consisting of oxazolidin-3-yl, 2,3-dihydroisoxazol-2-yl, isoxazol-2-yl, 1,2,3-oxadiazin-2-yl and morpholino; a member of cyclic amino groups having saturated and unsaturated monocyclic groups with one to three nitrogen atoms and one to two sulfur atoms as heteroatoms selected from the group consisting of thiozolidin-3-yl, isothiazolin-2-yl, thiomorpholino, or dioxothiomorpholino; a member of cyclic amino groups having saturated and unsaturated fused cyclic groups selected from the group consisting of indol-1-yl, 1,2-dihydrobenzimidazol-1-yl and perhydropyrrolo[1,2-a]pyrazin-2-yl; a member of cyclic amino groups having spirocyclic groups selected from the group consisting of 2-azaspiro[4.5]decan-2-yl; a member of cyclic amino groups having bridged heterocyclic groups selected from the group consisting of 2-azabicyclo[2.2.1]heptan-7-yl, which may optionally be substituted, and R$^3$ and R$^9$ each represent independently of one another hydrogen, $C_{1-8}$-alkyl or aryl-$C_{1-2}$-alkyl, $C_{3-6}$-cycloalkyl-$C_{1-2}$-alkyl, and R$^6$ and R$^{12}$ each represent indepenenty of one another hydrogen, straight-chain or branched $C_{1-8}$-alkyl, $C_{1-8}$-alkenyl, $C_{3-6}$-cycloalkyl, $C_{3-6}$-cycloalkyl-$C_{1-2}$-alkyl, aryl-$C_{1-2}$-alkyl, hetaryl-$C_{1-2}$-alkyl, aryl or hetaryl, cycloalkyl-$C_{1-2}$-alkyl, aryl-$C_{1-2}$-alkyl, hetaryl-$C_{1-2}$-alkyl, aryl or hetaryl, selected from the group consisting of benzyl, furyl and pyridinyl groups each of which is optionally substituted, and $X^1$, $X^2$, $X^3$ and $X^4$ each represent independently of one another oxygen or sulfur, it being necessary for at least one of the radicals $X^1$, $X^2$, $X^3$ and $X^4$ of the thiodepsipeptide to represent sulfur, and their optical isomers and racemates.

2. Process for preparing the thiodepsipeptides of claim 1 and salts thereof

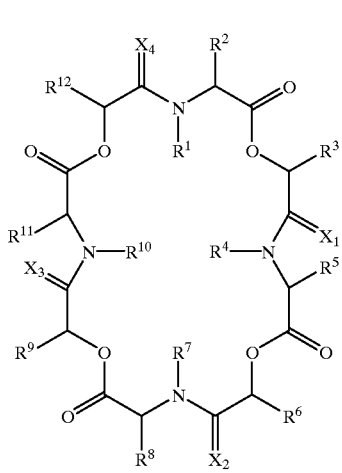

in which

R$^1$, R$^4$, R$^7$ and R$^{10}$ each represent independently of one another hydrogen, straight-chain or branched $C_{1-4}$-alkyl, and $R^2$, $R^5$, $R^8$ and $R^{11}$ each represent independently of one another hydrogen, straight-chain or branched $C_{1-8}$-alkyl, $C_{1-8}$-alkenyl, $C_{3-6}$-cycloalkyl, $C_{3-6}$-cycloalkyl-$C_{1-2}$-alkyl, aryl-$C_{1-2}$-alkyl, hetaryl-$C_{1-2}$-alkyl, aryl or hetaryl, selected from the group consisting of benzyl, furyl and pyridinyl groups, each of which is optionally substituted, and $R^9$ and $R^{10}$ together with the atoms that they are attached to represent a 5- or 6membered ring which may optionally be substituted, and $R^{10}$ and $R^{11}$ together with the atoms that they are attached to represent a 5- or 6-membered ring which may optionally be interrupted by oxygen, sulfur, sulfoxy or sulfonyl which is a member of cyclic amino groups having saturated and unsaturated monocyclic groups with a nitrogen atom as heteroatom selected from the group consisting of 1-azetidinyl, pyrrolidino, 2-pyrrolin-1-yl, 1-pyrrolyl, piperidino, 1,4dihydropyrazin-1-yl, 1,2,5,6-tetrahydropyrazin-1-yl, 1,4dihydropyridin-1-yl, 1,2,5,6-tetrahydropyridin-1-yl or homopiperidinyl; a member of cyclic amino groups having saturated and unsaturated monocyclic groups with two or more nitrogen atoms as heteroatoms selected from the group consisting of 1-midazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropyrimidin-1-yl, perhydropyrimidin-1-yl and 1,4-dlazacycloheptan-1-yl; a member of cyclic amino groups having saturated and unsaturated monocyclic groups with one or two oxygen atoms and one to 3 nitrogen atoms as heteroatoms selected from the group consisting of oxazolidin-3-yl, 2,3dihydroisoxazol-2-yl, isoxazol-2-yl, 1,2,3-oxadiazin-2-yl and morpholino; a member of cyclic amino groups having saturated and unsaturated monocyclic groups with one to three nitrogen atoms and one to two sulfur atoms as heteroatoms selected from the group consisting of thiozolidln-3-yl, isothiazolin-2-yl, thiomorpholino, or dioxothiornorpholino; a member of cyclic amino groups having saturated and unsaturated fused cyclic groups selected from the group consisting of indol-1-yl, 1,2-dihydrobenzimidazol-1-yl and perhydropyrrolol[1,2-a]pyrazin-2-yl; a member of cyclic amino groups having spirocyclic groups selected from the group consisting of 2-azaspiro[4.5]decan-2-yl; a member of cyclic amino groups having bridged heterocyclic groups selected from the group consisting of 2-azabicyclo[2.2.1]heptan-7-yl, which may optionally be substituted, and $R^3$ and $R^9$ each represent independently of one another hydrogen, $C_{1-8}$-alkyl or aryl-$C_{1-2}$-alkyl, $C_{3-6}$-cycloalkyl-$C_{1-2}$-alkyl, and $R^6$ and $R^{12}$ each represent independently of one another hydrogen, straight-chain or branched $C_{1-8}$-alkyl, $C_{1-8}$-alkenyl, $C_{3-6}$-cyloalkyl, $C_{3-6}$-cycloalkyl-$C_{1-2}$-alkyl, aryl-$C_{1-2}$-alkyl, hetaryl-$C_{1-2}$-alkyl, aryl or hetaryl, selected from the group consisting of benzyl, turyl and pyridinyl groups, each of which is optionally substituted, and $X^1$, $X^2$, $X^3$ and $X^4$ each represent independently of one another oxygen or sulfur, it being necessary for at least one of the radicals $X_1$, $X^2$, $X^3$ and $X^4$ of the thiodepsipeptide to represent sulfur, and their optical isomers and racemates,
comprising thionating the depsipeptides of the general formula (II) and salts thereof

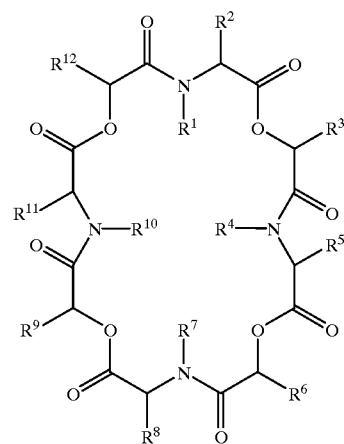

(II)

in which
$R^1$ to $R^{12}$ and $X^1$ to $X^4$ are each as defined above,
in the presence of a suitable sulfurizing agent and in the presence of a suitable diluent.

3. Thiodepsipeptides comprising amino acids, hydroxythiocarboxylic acids and optionally hydroxycarboxylic acids as ring building blocks and having 24 ring atoms of claim 1 and salts thereof

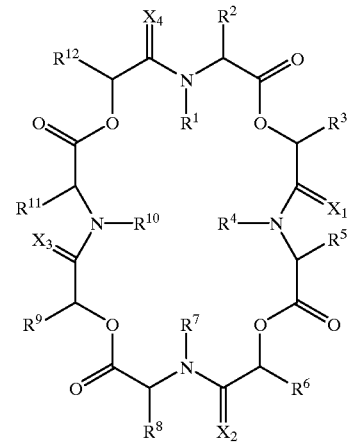

(I)

in which
$R^1$, $R^4$, $R^7$ and $R^{10}$ each represent straight-chain or branched $C_{1-4}$-alkyl, and $R^2$, $R^5$, $R^8$ and $R^{11}$ each represent $C_{1-4}$-alkyl, and $R^3$ and $R^9$ each represent independently of one another $C_{1-4}$-alkyl or aryl-$C_{1-2}$-alkyl, and $R^6$ and $R^{12}$ each represent independently of one another $C_{1-4}$-alkyl, hetaryl-$C_{1-2}$-alkyl, $C_{1-4}$-alkoxycarbonylmethyl, aryl-$C_{1-2}$-alkyl, suitable substituents including hydrogen, halogen, cyano, carbamoyl, $C_{1-4}$-alkyl, hydroxyl or hydroxyl carrying a protecting group, $C_{1-8}$-alkoxy, $C_{1-4}$-alkoxy-$C_{1-4}$-alkoxy, $C_{2-4}$-alkenyloxy hetaryl-$C_{1-4}$-alkoxy where the heterocycles may in turn be substituted, nitro, amino or amino carrying a protecting group, amino-$C_{1-6}$-alkoxy or amino-$C_{1-6}$-alkoxy carrying a protecting group, n-mono-$C_{1-6}$-alkyl-amino-$C_{1-6}$-alkoxy, N-methylamino-N,N-di-$C_{1-6}$-alkylamino-$C_{1-6}$-alkoxy, N,N-di-[($C_{1-6}$-alkoxy-$C_{1-6}$-alkyl)]amino-$C_{1-6}$-alkoxy, $C_{1-4}$-alkylamino, $C_{1-4}$-dialkylamino, N,N-di[($C_{1-6}$-alkoxy-$C_{1-6}$-alkyl)]amino-sulfonyl, $C_{1-4}$-dialkylamino-sulfonyl, sulfamidyl, $C_{3-7}$-cycloalkylamino-$C_{1-6}$-alkylamino-sulfonyl, $C_{3-7}$-cycloalkyl-amino-$C_{1-6}$-alkoxy, $C_{3-7}$-cycloalkylamino-sulfonyl, $C_{3-7}$-cycloalkylamino- where each cycloalkyl may contain one or more nitrogen atoms as ring-forming atoms and additionally oxygen or sulfur atoms, and (i)
$X^1$ represents sulfur,
$X^2$, $X^3$ and $X^4$ of the thiodepsipeptide each represent independently of one another oxygen or sulfur, or
(ii)
$X^2$ represents sulfur,
$X^1$, $X^3$ and $X^4$ of the thiodepsipeptide each represent independently of one another oxygen or sulfur, or
(iii)
$X^3$ represents sulfur,
$X^1$, $X^2$ and $X^4$ of the thiodepsipeptide each represent independently of one another oxygen or sulfur, or
(iv)
$X^4$ represents sulfur,
$X^1$, $X^2$ and $X^3$ of the thiodepsipeptide each represent independently of one another oxygen or sulfur, and their optical isomers and racemates.

4. A method for controlling endoparasites in an animal or human comprising administering thereto cyclic thiodepsipeptides of the formula (I) according to claim 1.

5. A method for preparing an endoparasitical composition comprising formulating cyclic thiodepsipeptides of the formula (I) according to claim 1.

6. Endoparasitical compositions comprising cyclic thiodepsipeptides of the formula (I) according to claim 1, optionally with diluents and additives.

7. The thiodepsipeptides of claim 3 wherein $R^1$, $R^4$, $R^7$, and $R^{10}$ each represent methyl.

8. The thiodepsipeptides of claim 3 wherein $R^2$, $R^5$, $R^8$, and $R^{11}$ each represent isobutyl.

9. The thiodepsipeptides of claim 3 wherein $R^3$ and $R^9$ each represent independently of one another benzyl.

10. The thiodepsipeptides of claim 3 wherein $R^6$, and $R^{12}$ each represent independently bnyzyl.

* * * * *